(12) United States Patent
Karlstrom et al.

(10) Patent No.: US 9,000,185 B2
(45) Date of Patent: *Apr. 7, 2015

(54) CYCLOALKYL ETHER COMPOUNDS AND THEIR USE AS BACE INHIBITORS

(71) Applicant: AstraZeneca AB, Sodertalje (SE)

(72) Inventors: Sofia Karlstrom, Cheshire (GB); Peter Soderman, Cheshire (GB); Britt-Marie Swahn, Cheshire (GB); Laszlo Rakos, Cheshire (GB); Liselotte Ohberg, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,740

(22) Filed: Jun. 13, 2013

(65) Prior Publication Data

US 2013/0345272 A1 Dec. 26, 2013

Related U.S. Application Data

(60) Provisional application No. 61/661,923, filed on Jun. 20, 2012.

(51) Int. Cl.
*C07D 235/02* (2006.01)
*A61K 31/428* (2006.01)
*A61K 45/06* (2006.01)

(52) U.S. Cl.
CPC ............ *C07D 235/02* (2013.01); *A61K 31/428* (2013.01); *A61K 45/06* (2013.01)

(58) Field of Classification Search
USPC ...................................... 548/301.1
See application file for complete search history.

(56) References Cited

U.S. PATENT DOCUMENTS

| 8,415,483 | B2 * | 4/2013 | Csjernyik et al. .......... 548/301.1 |
| 2013/0210837 | A1 | 8/2013 | Csjernyik et al. |
| 2013/0345246 | A1 | 12/2013 | Karlstrom et al. |
| 2013/0345247 | A1 | 12/2013 | Karlstrom et al. |
| 2013/0345248 | A1 | 12/2013 | Karlstrom et al. |
| 2014/0031379 | A1 | 1/2014 | Bohlin et al. |

FOREIGN PATENT DOCUMENTS

| WO | WO 2005094822 | 10/2005 |
| WO | WO 2006138264 | 12/2006 |
| WO | WO 2007076247 | 7/2007 |
| WO | WO 2007100536 | 9/2007 |
| WO | WO 2008076043 | 6/2008 |
| WO | WO 2009100169 | 8/2009 |
| WO | WO 2010013794 | 2/2010 |
| WO | WO 2010021680 | 2/2010 |
| WO | WO 2010030954 | 3/2010 |
| WO | WO 2010105179 | 9/2010 |
| WO | WO 2011002407 | 1/2011 |
| WO | WO 2011002408 | 1/2011 |
| WO | WO 2011106414 | 9/2011 |
| WO | WO 2011123674 | 10/2011 |
| WO | WO 2011130741 | 10/2011 |
| WO | WO 2012019056 | 2/2012 |
| WO | WO 2012040641 | 3/2012 |
| WO | WO 2012071458 | 5/2012 |
| WO | WO 2012087237 | 6/2012 |

OTHER PUBLICATIONS

Thompson et al., Current Medicinal Chemistry, Oct. 2002, 9(19), pp. 1751-1762.*

Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007, pp. 188-199.

Hong et al., "Structure of the Protease Domain of Memapsin 2 (β-Secretase) Complexed with Inhibitor," Science 2000, 290, 5489, pp. 150-153.

John et al, "Human β-Secretase (BACE) and BACE Inhibitors," Journal of Medicinal Chemistry, 2003, 46, pp. 4625-4630.

Roberds et al, "BACE knockout mice are healthy despite lacking the primary B-secretase activity in brain: implications for Alzheimer's disease therapeutics," Human Molecular Genetics, 2001, 10, pp. 1317-1324.

Sinha et al, "Purification and cloning of amyloid precursor protein β-secretase from human brain," Nature, 1999, 402, pp. 537-540.

* cited by examiner

*Primary Examiner* — Laura L. Stockton
(74) *Attorney, Agent, or Firm* — Ropes & Gray LLP

(57) ABSTRACT

Cycloalkyl ether compounds, therapeutically acceptable salts thereof, processes for preparation thereof, therapeutic uses of such compounds for treating Aβ-related pathologies such as Down's syndrome, β-amyloid angiopathy, Alzheimer's disease, memory loss, attention deficit symptoms associated with Alzheimer's disease, neurodegeneration associated with diseases such as Alzheimer's disease or dementia including dementia of mixed vascular and degenerative origin, presenile dementia, senile dementia and dementia associated with Parkinson's disease, progressive supranuclear palsy or cortical basal degeneration and pharmaceutical compositions containing such compounds.

7 Claims, No Drawings

CYCLOALKYL ETHER COMPOUNDS AND THEIR USE AS BACE INHIBITORS

CROSS-REFERENCE TO RELATED APPLICATIONS

This application claims the benefit under 35 U.S.C. §119 (e) to U.S. Application No. 61/661,923 filed on Jun. 20, 2012, which is incorporated herein by reference.

FIELD OF THE INVENTION

The present invention relates to cycloalkyl ether compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, presenile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, presenile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

DETAILED DESCRIPTION OF THE INVENTION

The present invention is directed to compounds according to formula (I):

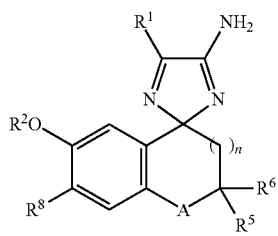

wherein
A is —O—, or —CH$_2$—;
n is 0 or 1;
R$^1$ is C$_{1-6}$alkyl or C$_{1-6}$haloalkyl;
R$^2$ is C$_{1-6}$alkyl, or C$_{1-6}$haloalkyl; wherein said C$_{1-6}$alkyl or C$_{1-6}$haloalkyl is substituted with one to three groups independently selected from C$_{3-6}$cycloalkyl or C$_{3-6}$halocycloalkyl;
R$^5$ and R$^6$ is independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano, or OR$^9$;
or R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl, C$_{1-6}$haloalkyl, cyano, or OR$^7$;
R$^7$ is independently hydrogen, C$_{1-6}$alkyl, C$_{1-6}$haloalkyl, or C$_{0-6}$alkylC$_{3-6}$cycloalkyl;
R$^8$ is hydrogen, halogen or methyl;
as a free base or a pharmaceutically acceptable salt thereof.

In a particular embodiment the invention is directed to a compound of according to formula I selected from the group consisting of:

(1r,4r)-4-Methoxy-5''-methyl-6'-[(1-methylcyclopropyl)methoxy]-3'H-dispiro[cyclohexane-1,2'-indene-1',2''-imidazol]-4''-amine;

(1r,4r)-6'-[(3,3-Difluorocyclobutyl)methoxy]-4-methoxy-5''-methyl-3'H-dispiro[cyclohexane-1,2'-indene-1',2''-imidazol]-4''-amine;

(1r,4r)-6'-(Cyclopropylmethoxy)-4-methoxy-5''-methyl-3'H-dispiro[cyclohexane-1,2'-indene-1',2''-imidazol]-4''-amine;

(1r,1'R,4R)-6'-(Cyclopropylmethoxy)-4-methoxy-5''-methyl-3'H-dispiro[cyclohexane-1,2'-indene-1',2''-imidazol]-4''-amine;

(1r,1'S,4S)-6'-(Cyclopropylmethoxy)-4-methoxy-5''-methyl-3'H-dispiro[cyclohexane-1,2'-indene-1',2''-imidazol]-4''-amine;

(1r,4r)-6'-[(2,2-Difluorocyclopropyl)methoxy]-4-methoxy-5''-methyl-3'H-dispiro[cyclohexane-1,2'-indene-1',2''-imidazol]-4''-amine;

(1r,4r)-6'-(Cyclobutylmethoxy)-4-methoxy-5''-methyl-3'H-dispiro[cyclohexane-1,2'-indene-1',2''-imidazol]-4''-amine;

(1r,1'R,4R)-6'-(Cyclobutylmethoxy)-4-methoxy-5''-methyl-3'H-dispiro[cyclohexane-1,2'-indene-1',2''-imidazol]-4''-amine;

(1r,1'S,4S)-6'-(Cyclobutylmethoxy)-4-methoxy-5''-methyl-3'H-dispiro[cyclohexane-1,2'-indene-1',2''-imidazol]-4''-amine, and (1r,4r)-6'-(2-Cyclopropylethoxy)-4-methoxy-5''-methyl-3'H-dispiro[cyclohexane-1,2'-indene-1',2''-imidazol]-4''-amine, or a pharmaceutical salt of any foregoing compound.

The present invention relates to the use of compounds according to the present invention as well as to the salts thereof. Salts for use in pharmaceutical compositions will be pharmaceutically acceptable salts, but other salts may be useful in the production of the compounds according to the present invention.

The compounds according to the present invention may be administered in the form of a prodrug which is broken down in the human or animal body to give a compound according to the present invention. Examples of prodrugs include in vivo hydrolysable esters of a compound according to the present invention. An in vivo hydrolysable (or cleavable) ester of a compound according to the present invention that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

The present invention further includes all tautomeric forms of compounds of the invention.

As used herein, "tautomer" means other structural isomers that exist in equilibrium resulting from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compounds will depend on the specific application of that radio-labeled compound. For example, for in vitro receptor labelling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect, the invention relates to a compound according to the present invention, or a pharmaceutically acceptable salt thereof, for use as a medicament, e.g. for treatment or prevention of Aβ-related pathologies.

In another aspect, the invention relates to the use of a compound according to the present invention, or a pharmaceutically acceptable salt thereof, in the manufacture of a medicament for treatment or prevention of Aβ-related pathologies.

In another aspect, the invention relates to a method of treating or preventing Aβ-related pathologies in a mammal, such as a human being, comprising administering to a mammal in need thereof a therapeutically effective amount of a compound according to the present invention, or a pharmaceutically acceptable salt thereof.

The compounds of the invention, and their pharmaceutically acceptable salts, thereby provide methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy traumatic brain injury and cortical basal degeneration.

In another aspect, the invention relates to a pharmaceutical composition comprising as active ingredient a therapeutically effective amount of a compound according to the present invention, or a pharmaceutically acceptable salt thereof, in association with at least one pharmaceutically acceptable excipient, carrier or diluent.

In another aspect, the invention relates to a method of inhibiting activity of BACE with a compound according to the present invention.

In another aspect, the invention relates to a method of treating or preventing an Aβ-related pathology in a mammal, such as a human being, comprising administering to said patient a therapeutically effective amount of a compound according to the present invention, or a pharmaceutically acceptable salt thereof, and at least one cognitive enhancing agent, memory enhancing agent, or cholineesterase inhibitor, wherein said Aβ-related pathology is Alzheimer's disease.

In another aspect, the invention relates to a pharmaceutical composition comprising (i) a compound according to the present invention, or a pharmaceutically acceptable salt thereof, (ii) an additional therapeutic agent, or a pharmaceutically acceptable salt thereof, and (iii) pharmaceutically acceptable excipients, carriers or diluents.

In another aspect, the invention relates to a pharmaceutical composition comprising (i) a compound according to the present invention, or a pharmaceutically acceptable salt thereof, (ii) at least one agent selected from the group consisting of cognitive enhancing agents, memory enhancing agents and choline esterase inhibitors, and (iii) pharmaceutically acceptable excipients, carriers or diluents.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYE or RAZADYNE), rivastigmine (EXELON), tacrine (COGNEX) and memantine (NAMENDA, AXURA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ the compounds of this invention within the dosage range described herein and the other pharmaceutically active compound or compounds within approved dosage ranges and/or the dosage described in the publication reference.

Preparation of Compounds

The compounds of the present invention can be prepared as a free base or a pharmaceutically acceptable salt thereof by the processes described herein. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999. It is understood that microwaves (MW) can alternatively be used for the heating of reaction mixtures. Another aspect of the present invention provides a process for preparing a compound of formula (I), or a pharmaceutically acceptable salt thereof, wherein, unless specified otherwise, $R^1$-$R^8$, n and A are defined as for formula (I) above, or are groups that can be converted into $R^1$-$R^8$, or A in subsequent transformations. $R^9$ is defined as $OR^2$ or is a group, such as a leaving group as for example a halogen, that can be converted into a group $OR^2$ in a subsequent transformation. A compound of formula (X) may be equivalent to a compound of formula (I). LG represents a leaving group such as halogen (such as chlorine, bromine or iodine) or an alkyl-, aryl- or haloalkyl-sulfonate (such as triflate) and PG represents a protecting group. Said process comprises:

Method (i): Formation of a Corresponding Compound of Formula (IIIa)

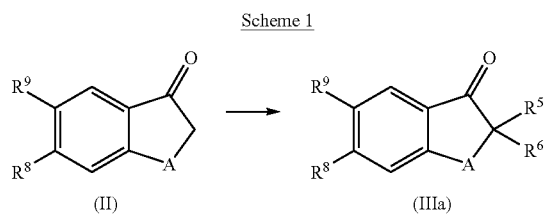

Scheme 1

(II)    (IIIa)

A ketone of formula (II), is treated with a suitable base such as sodium hydride, KOtBu, or LDA in presence of a suitable electrophile such as methyl acrylate, (bis-substituted) alkyl halide, triflate or mesylate to give a compound of formula (Ma) (Scheme 1). The reaction may be performed at a temperature range between 0° C. and +90° C., in a suitable solvent, such as tetrahydrofuran, 2-Me THF or dimethylformamide. Alkyations may be carried out in a sequential way with intermediates isolated and purified or in a one-pot stepwise fashion. If the reactions yield a product substituted with a ester, olefin, cyano, sulfone, sulfonium donor the like, it could optionally be reacted further by Dieckman cyclization, RCM, nucleophilic substitution or cycloaddition. The resulting spirocyclic ring may optionally contain one or more substituent which may be further converted by known functional group transformations, such as decarboxylation, reduction of a ketone to an alcohol and conversion of said alcohol to an ether.

Method (ii): Formation of a Corresponding Compound of Formula (IIIa)

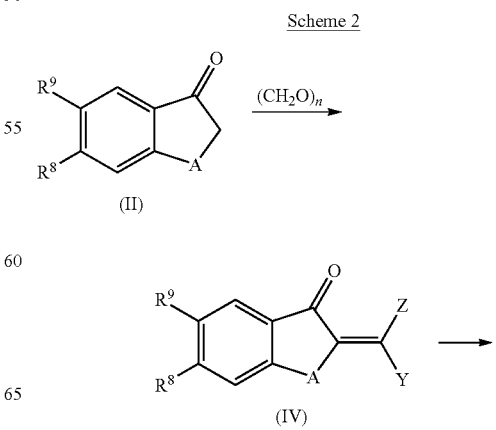

Scheme 2

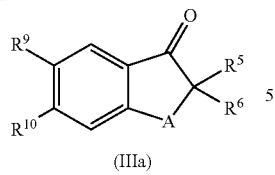

(IIIa)

A ketone of formula (II), is reacted with an aldehyde or ketone such as formaldehyde in a temperature range between room temperature and +100° C. in presence of N-Methylanilinium trifluoroacetate, in a suitable solvent such THF, benzene or toluene (Scheme 2). The intermediate (IV), wherein Z and Y are defined as for example hydrogen or alkyl, can be reacted with various dienes such as (buta-1,3-dien-2-yloxy)trimethylsilane utilizing the Diels-Alder reaction in a temperature range between 0° C. and +90° C. optionally in a sealed tube. The reaction can be carried out neat or in a suitable solvent such as dichloromethane, benzene, toluene, THF or 2-Me THF. A Lewis acid or any other agents that may assist the reaction can be added to yield enriched enantiomers or diastereomers. The resulting spirocyclic ring may optionally contain one or more substituent which may be further converted by known functional group transformations, such as decarboxylation, reduction of a ketone to an alcohol and conversion of said alcohol to an ether.

Method (iii) Formation of a Corresponding Compound of Formula (VII)

Scheme 3

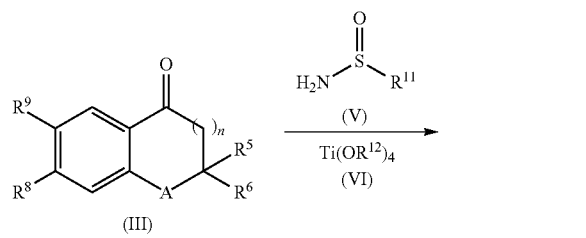

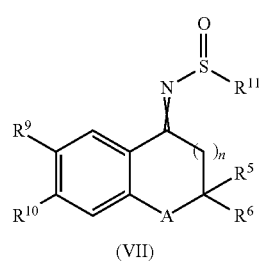

(VII)

A compound of formula (VII) may be obtained by reacting a compound of formula (III) with a compound of formula (V) (Scheme 3), wherein $R^{11}$ is alkyl (such as for example tert-butyl). The reaction is performed in the presence of a suitable Lewis acid, such as a compound of formula (VI), wherein $R^{12}$ is alkyl (such as ethyl or isopropyl). The reaction is performed in a suitable solvent (such as dichloromethane, 2-methyl-tetrahydrofuran or tetrahydrofuran) at a temperature between room temperature and reflux temperature, optionally with azeotropic distillation to remove an alcohol formed in the reaction.

Method (iv) Formation of a Corresponding Compound of Formula (X)

Scheme 4

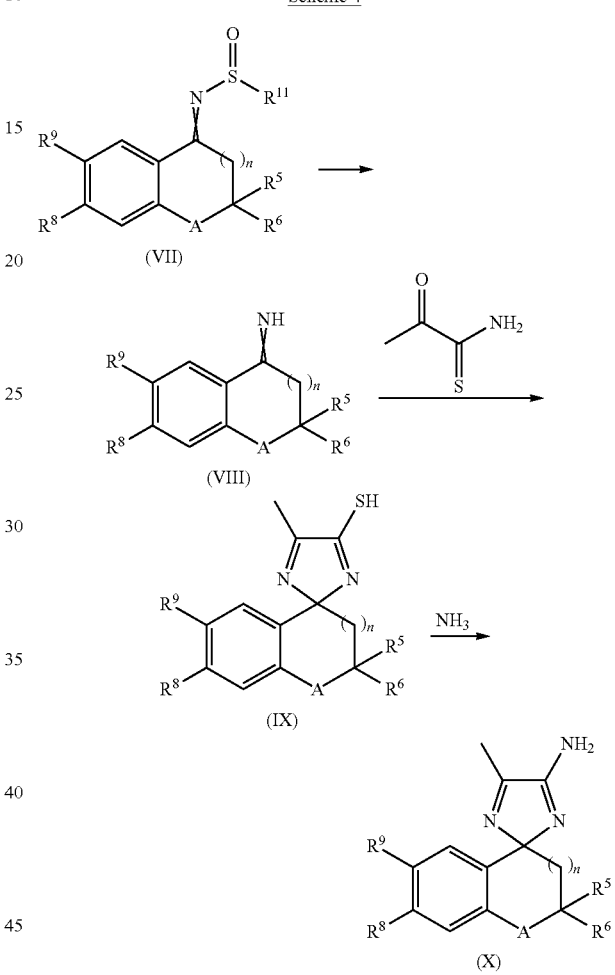

A compound of formula (VIII) may be obtained by reacting a compound (VII) (wherein $R^{11}$ is alkyl (such as for example tert-butyl). (Method (iii), formula VII), using a suitable method of removing the sulfonamide protecting group to form imine (VIII) (Scheme 4). A suitable method may be, but is not limited to, treating said compound VII with an acid such as hydrochloric acid under dry conditions in a suitable solvent (such as dioxane or tetrahydrofuran). Compound (VIII) may be isolated or reacted further without isolation. A compound of formula (VIII) is further reacted with 2-oxopropane thioamide (described in Asinger et al. *Justus Liebigs Annalen der Chemie* 1971, vol 744, p. 51-64) optionally in the presence of triethyl orthoformate, in a solvent such as methanol at a temperature between room temperature and reflux temperature, optionally under Dean-Stark conditions, to yield a compound of formula (IX). The transformation to a compound of formula (X) may be performed by reacting the intermediate of formula (IX) with ammonia. If 2-oxopropane thioamide is exchanged for 2-oxobutanethioamide in the process described by Scheme 4, the compounds of formula (IXb) and (Xb) will be obtained instead of (IX) and (X).

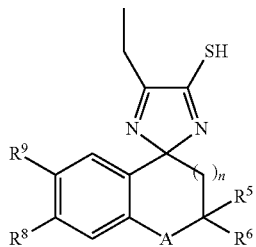
(IXb)

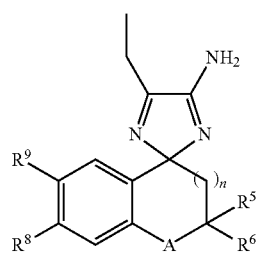
(Xb)

Method (v) Formation of a Corresponding Compound of Formula (I)

Scheme 5

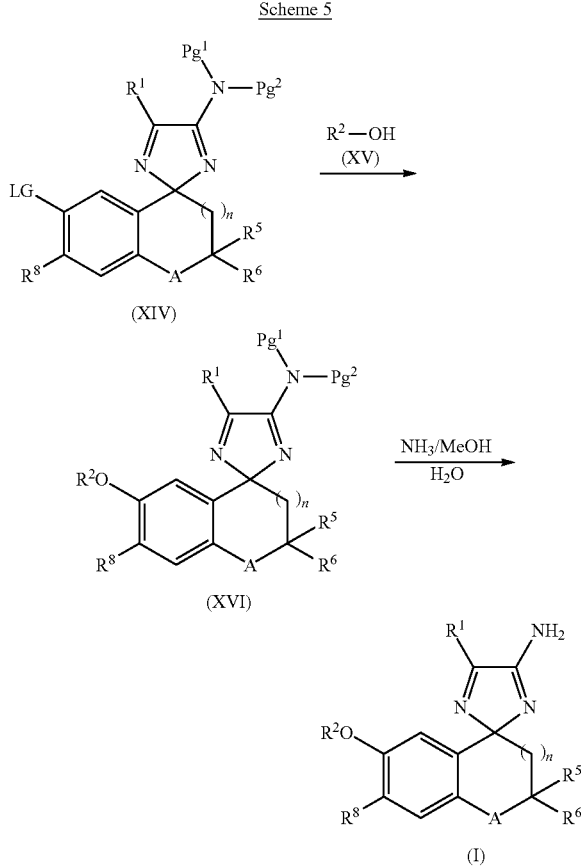

A compound of formula (XVI) may be prepared by reacting a compound of formula (XIV), wherein LG represents a leaving group, such as a halogen, (such as iodide or bromide), $Pg^1$ and $Pg^2$ represents hydrogen and/or a suitable protecting group such as tert-butoxycarbonyl, with an alcohol of formula (XV) in the presence of a suitable palladium catalyst such as palladium(II) acetate, optionally in the presence of a suitable ligand such as di-tert-butyl(2',4',6'-triisopropyl-3-methoxy-6-methylbiphenyl-2-yl)phosphine or 2-(di-t-butylphosphino)-1,1'-binaphthyl (Scheme 5). The reaction is performed in the presence of a suitable base such as cesium carbonate in a suitable solvent such as THF, 2-methyl-tetrahydrofuran or toluene at a temperature between 20° C. and 160° C. The compound of formula (I) may be obtained from compound of formula (XVI) wherein $Pg^1$ and/or $Pg^2$ is tert-butoxycarbonyl, by reacting with a solution of $NH_3$, such as in methanol, in the presence of water, at a temperature between 60° C. and 100° C.

Compounds of formula (II), (V), (VI), (XIII), and (XV) are commercially available compounds, or are known in the literature, or may be prepared by standard processes known in the art.

General Methods

All solvents used were of analytical grade and commercially available anhydrous solvents were routinely used for reactions. Starting materials used were available from commercial sources, or prepared according to literature procedures. Room temperature refers to 20 to 25° C. Solvent mixture compositions are given as volume percentages or volume ratios.

MW heating was performed in a Biotage Creator, Initiator or Smith Synthesizer Single-mode MW cavity producing continuous irradiation at 2450 MHz. It is understood that microwaves can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS analyses: High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS analyses: Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative chromatography was run on a Waters Fraction-Lynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC analyses: Supercritical Fluid Chromatography (SFC) was performed on a straight phase column. A isocratic flow was applied using mobile phase A ($CO_2$) and for example mobile phase B (MeOH, EtOH or IPA).

Straight phase HPLC analyses: High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS) for accurate mass measurements was performed on a Waters Synapt-G2 mass spectrometer equipped with a LockSpray source and connected to an Acquity UPLC system with a PDA detector and an Acquity UPLC BEH C18 column. The measured mass confirmed the elemental composition within 3 ppm.

Abbreviations
ACN acetonitrile
aq aqueous
Atm atmospheric pressure
Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone
DCM dichloromethane
DEA diethylamine
DIBAL-H diisobutylaluminium hydride
DIPEA diisopropylethylamine
DMAP 4-Dimethylaminopyridine
DME 1,2-dimethoxyethane
DMF N,N-dimethyl formamide
DMSO dimethyl sulfoxide
dppf 1,1'-bis(diphenylphosphino)ferrocene
$Et_2O$ diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW microwave(s)
$NH_4OAc$ ammonium acetate
NMR nuclear magnetic resonance
ox oxidation
Psi pounds per square inch
quant. quantitative
RCM ring closing metathesis
r.t. room temperature
sat. saturated
SFC supercritical fluid chromatography
TFA trifluoroacetic acid
THF tetrahydrofuran
TLC thin layer chromatography
TMEDA tetramethylethylenediamine
UPLC ultra performance liquid chromatography
2-Me THF 2-methyl tetrahydrofuran Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acdlabs.com, or Lexichem, version 1.9, software from OpenEye.

INTERMEDIATES

Intermediate 1

2-Oxopropanethioamide

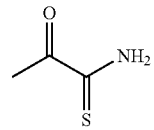

To a −10° C. solution of THF (1700 mL) and acetyl cyanide (250 mL, 3.15 mol) was $H_2S$ bubbled for approx 45 min. The bubbling was stopped, and the solution was stirred until the temp. was −10° C. More $H_2S$ was bubbled until the temperature was stable at −10° C. Triethylamine (2.2 mL, 15.8 mmol) in THF (20 mL) was added dropwise (very exothermic reaction) at such a rate that temp. was kept between 0° C. and −3° C. After addition was completed, the temp. was set to +4° C. and the mixture was stirred overnight. Nitrogen was flushed through the reaction for 30 min and the mixture was concentrated to give the title product (319 g, 98% yield). $^1$H NMR (500 MHz, $CDCl_3$) ppm 2.67 (s, 3H), 7.30-7.81 (m, 1H), 7.97-8.52 (m, 1H); $^{13}$C NMR (126 MHz, $CDCl_3$) ppm 25.1, 190.8, 192.5; MS (ES+) m/z 104 $[M+H]^+$.

Intermediate 2

6'-Bromospiro[cyclohexane-1,2'-indene]-1',4(3'H)-dione

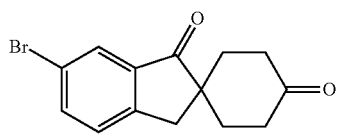 [SMILES: O=C1CCC2(CC1)Cc1ccc(Br)cc1C2=O]

Method A

Potassium tert-butoxide (7.50 g, 66.8 mmol) was added in portions to 6-bromo-2,3-dihydro-1H-inden-1-one (11.8 g, 55.7 mmol) and methyl acrylate (11.1 mL, 123 mmol) in THF (55 mL) under cooling in an ice-bath. The mixture was stirred for 1.5 h at r.t. Water (80 mL) and KOH (3.12 g, 55.7 mmol)

was added and the mixture was heated to 75° C. and then at 60° C. overnight. The mixture was cooled to 0° C., and the formed precipitate was filtered off and dried in vacuo to give the title compound (11.69 g, 72% yield). $^1$H NMR (500 MHz, CDCl$_3$) δ ppm 1.83-1.92 (m, 2H), 2.15-2.27 (m, 2H), 2.40-2.50 (m, 2H), 2.71 (dt, 2H), 3.17 (s, 2H), 7.39 (d, 1H), 7.75 (dd, 1H), 7.92 (d, 1H); MS (ES+) m/z 293 [M+H]$^+$.

Method B

6-Bromo-2,3-dihydro-1H-inden-1-one (800 g, 3.79 mol) and methyl acrylate (787 mL, 8.72 mol) in 2-Me THF (4 L) were stirred at 28° C. Potassium tent-pentoxide solution in toluene (1.7 M, 2.68 L, 4.55 mol) was added dropwise keeping the temperature between 30° C. and 43° C. The mixture was stirred for 0.5 h at 25° C. Water (4 L) was added and after 10 min were KOH (383 g, 6.82 mol) added. The mixture was heated to reflux and the organic solvent was distilled off during 4 h. The mixture was cooled to 10° C., and the formed precipitate was filtered off and dried in vacuo to give the title compound (837 g, 75% yield). $^1$H NMR (500 MHz, DMSO-d$_6$) ppm 1.74-1.85 (m, 2H), 1.94 (m, 2H), 2.34 (m, 2H), 2.52-2.60 (m, 2H), 3.27 (s, 2H), 7.60 (d, 1H), 7.79-7.83 (m, 1H), 7.89 (m, 1H); MS (ES+) m/z 293 [M+H]$^+$.

Method C

Methyl acrylate (6.6 L, 73 mol) was charged gradually in three equal portions (each 2.2 L, 24.6 mol) to a mixture of 6-bromo-1-indanone (8.00 kg, 37.9 mol), THF (16 L) and potassium tert-butoxide (210 g, 1.87 mol) at about 20-30° C. Additional potassium tert-butoxide (86 g, 0.77 mol), dissolved in THF (0.39 L), was charged after the first portion of methyl acrylate. More potassium tert-butoxide (86 g, 0.77 mol), dissolved in THF (0.39 L), was charged after the second portion of methyl acrylate. Further potassium tert-butoxide (4.64 kg, 41.3 mol) solution in THF (21 L) was then charged gradually at about 20-30° C. Solvent (21.5 L) was distilled off at about 65° C. and then a mixture of water (49 L) and 50%. aq KOH (2.3 L, 30 mol) was added over about 10 min. at below 60° C. The reaction was held at 60° C. for about 6 h., then cooled to 20° C. over 1 h. and then filtered after holding at 20° C. for about 12 h. The solids were washed with a mixture of water (8 L) and THF (4 L), and then dried to give the title compound (7.47 kg, at 92% w/w NMR assay, 23.4 mol, 62% yield): $^1$HNMR (500 MHz, DMSO-d$_6$) δ ppm 1.78-1.84 (m, 2H), 1.95 (td, 2H), 2.32-2.38 (m, 2H), 2.51-2.59 (m, 2H), 3.27 (s, 2H), 7.60 (d, 1H), 7.81 (m, 1H), 7.89 (m, 1H).

Intermediate 3

6'-Bromo-4-hydroxyspiro[cyclohexane-1,2'-inden]-1'(3'H)-one

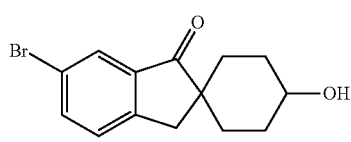

Method A

6'-Bromospiro[cyclohexane-1,2'-indene]-1',4(3'H)-dione (Intermediate 2, 6.1 g, 20.8 mmol) was dissolved in THF (220 mL) and cooled to −65° C. Sodium borohydride (0.354 g, 9.36 mmol) was added and the cooling bath was removed. The mixture was allowed to reach 0° C. (approx. 30 min). Water (10 mL) was added, and most of the organic solvent was removed by evaporation. The residue was partitioned between EtOAc (100 mL), and an aq. solution of NaCl (50 mL). The organic phase was dried (MgSO$_4$) and evaporated to give a product which was combined with additional product obtained in a similar way starting from 14.6 g of 6'-bromo-spiro[cyclohexane-1,2'-indene]-1',4(3'H)-dione. Purification was made by flash chromatography (120 g silica, gradient elution: CH$_2$Cl$_2$ to CH$_2$Cl$_2$/MeOH (90:10)) affording 13.6 g (66% yield) of the title compound. The obtained material consisted of an 80:20 mixture of isomer 1 and isomer 2. Analytical samples of the isomers were isolated by flash chromatography (heptane/EtOAc gradient) to yield:

Isomer 1: (1r,4r)-6'-Bromo-4-hydroxyspiro[cyclohexane-1,2'-inden]-1'(3'H)-one

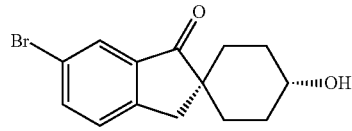 [SMILES: O=C1c2cc(Br)ccc2C[C@]12CC[C@@H](O)CC2]

$^1$H NMR (400 MHz, DMSO-d$_6$) δ ppm 1.20-1.43 (m, 4H), 1.49-1.62 (m, 2H), 1.79-1.89 (m, 2H), 2.99 (s, 2H), 3.39-3.50 (m, 1H), 4.68 (d, 1H), 7.56 (d, 1H), 7.76 (d, 1H), 7.85 (dd, 1H); MS (ES+) m/z 317 [M+Na]$^+$ and Isomer 2: (1s,4s)-6'-bromo-4-hydroxyspiro[cyclohexane-1,2'-inden]-1'(3'H)-one

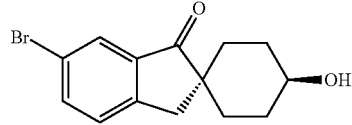

$^1$H NMR (400 MHz, DMSO-d$_6$) δ ppm 1.07-1.20 (m, 2H), 1.51-1.63 (m, 2H), 1.65-1.76 (m, 2H), 1.93 (td, 2H), 2.98 (s, 2H), 3.83 (d, 1H), 4.45 (d, 1H), 7.51-7.55 (m, 1H), 7.76 (d, 1H), 7.84 (dd, 1H); MS (ES+) m/z 317 [M+Na]$^+$.

Intermediate 3, isomer 1

Method B

To 6'-bromospiro[cyclohexane-1,2'-indene]-1',4(3'H)-dione (Intermediate 2, 50.5 g, 172 mmol) in DCM (250 mL), borane tert-butylamine complex (5.70 g, 65.5 mmol) in DCM (50 mL) was slowly charged at 0° C. After 40 min concentrated HCl (20 mL) followed by 20% NaCl (70 mL) were charged. The mixture was allowed to reach r.t. and was stirred for 30 min. The phases were separated and to the water phase were DCM (40 mL) and H$_2$O (10 mL) charged. The organic phases were combined, concentrated and dried in vacuo overnight to give the title product (52.4 g, 100% yield) as a mixture of the title product (83% yield) and the other diastereomer (1s,4s)-6'-bromo-4-hydroxyspiro[cyclohexane-1,2'-inden]-1'(3'H)-one (17%): $^1$H NMR (500 MHz, CDCl$_3$, signals for both isomers) ppm $^1$H NMR (500 MHz, CDCl$_3$) δ ppm 1.39-1.50 (m, 3H), 1.67-1.85 (m, 3H) 2.05-2.12 (m, 2H) 2.96 (s, 0.34; H), 2.98 (s, 1.68; H), 3.76 (m, 0.83; H), 4.04 (m, 0.17; H), 7.34 (m, 1H) 7.70 (m, 1H) 7.88 (d, 1H); MS (ES+) m/z 295 [M+H]$^+$.

Intermediate 3, isomer 1

Method C

6'-Bromospiro[cyclohexane-1,2'-indene]-1',4(3'H)-dione (Intermediate 2, 750 g, 2.56 mol) and propan-2-ol (9.855 L) were heated to reflux and ground NaOH (100 g, 2.50 mol) was added in two portions to the mixture. The mixture was heated to reflux for 2 h. 5 L of solvent were removed by vacuum distillation. Toluene (2 L) was added and 2 L of solvent was removed by vacuum distillation. Toluene (3 L) followed by 2 M HCl (1.278 L, 2.56 mol) was added to the mixture under stirring. The phases were separated and the organic phase was washed with water (2.0 L). The organic phase was concentrated and toluene (2 L) was added and then the mixture was concentrated. 2-Me THF (1 L) was added and then 0.5 L of the solvent was removed by vacuum distillation, the resulting mixture was used in the next step. The title compound was a mixture with the diastereomer (1s,4s)-6'-bromo-4-hydroxyspiro[cyclohexane-1,2'-inden]-1'(3'H)-one in the ratio 7:3 (established by HPLC and NMR analysis): $^1$H NMR (500 MHz, CDCl$_3$, signals for both isomers) ppm 1.40-1.52 (m, 3H), 1.70-1.84 (m, 3H), 2.04-2.11 (m, 2H), 2.97 (s, 0.62; H), 3.00 (s, 1.38; H), 3.73-3.81 (m, 0.7; H), 4.04 (m, 0.3; H), 7.31-7.38 (m, 1H), 7.67-7.73 (m, 1H), 7.89 (m, 1H).

Intermediate 4

6'-Bromo-4-methoxyspiro[cyclohexane-1,2'-inden]-1'(3'H)-one

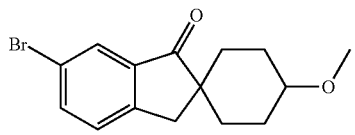

Method A

A mixture of isomers of 6'-bromo-4-hydroxyspiro[cyclohexane-1,2'-inden]-1'(3'H)-one (Intermediate 3, 12.7 g, 43.0 mmol) was dissolved in THF (210 mL) under N$_2$ and cooled to 0° C. Potassium tert-butoxide (5.79 g, 51.6 mmol) was added portionwise and the mixture was stirred at 0° C. for 25 min. Methyl iodide (4.30 mL, 68.8 mmol) was added. The cooling bath was removed, and the mixture was stirred at r.t. Additional potassium tert-butoxide (0.483 g, 4.30 mmol) was added twice, after 2 h and 3 h respectively, and then the mixture was stirred for 2 h. Water (100 mL) was added and the resulting solution was partitioned between aq. NaCl solution (200 mL), and EtOAc (200 mL). The aq. phase was extracted with another portion of EtOAc (100 mL). The combined organic phases were dried (MgSO$_4$) and evaporated to give 12.5 g (94% yield) of a mixture (approx. 80:20) of:

Isomer 1: (1r,4r)-6'-bromo-4-methoxyspiro[cyclohexane-1,2'-inden]-1'(3'H)-one

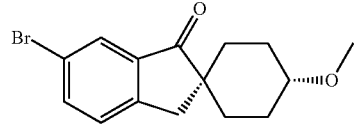 [SMILES: CO[C@H]1CC[C@]2(CC1)Cc1ccc(Br)cc1C2=O]

And Isomer 2: (1s,4s)-6'-bromo-4-methoxyspiro[cyclohexane-1,2'-inden]-1'(3'H)-one

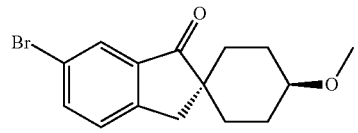 [SMILES: CO[C@H]1CC[C@@]2(CC1)Cc1ccc(Br)cc1C2=O]

$^1$H NMR (400 MHz, DMSO-d$_6$, signals for Isomer 1) δ ppm 1.20-1.32 (m, 2H), 1.40-1.48 (m, 2H), 1.51-1.62 (m, 2H), 1.97-2.07 (m, 2H), 3.00 (s, 2H), 3.15-3.23 (m, 1H), 3.26 (s, 3H), 7.56 (d, 1H), 7.77 (d, 1H), 7.86 (dd, 1H); MS (ES+) m/z 309 [M+H]$^+$.

Intermediate 4, Isomer 1

Method B (1r,4r)-6'-Bromo-4-hydroxyspiro[cyclohexane-1,2'-inden]-1'(3'H)-one (Intermediate 3, isomer 1, 50.9 g, 172 mmol) (containing 17% of (1s,4s)-6'-bromo-4-hydroxyspiro[cyclohexane-1,2'-inden]-1'(3'H)-one), methyl iodide (18.3 mL, 293 mmol) and 2-Me THF (360 mL) were heated to 30° C. under N$_2$. Potassium tent-pentoxide solution in toluene (1.7 M in toluene, 203 mL, 344 mmol) was added dropwise over 30 min. The mixture was allowed to reach r.t. and was stirred for 1 h. Water (250 mL) was added and after 10 min of stirring the phases were separated. The organic phase was washed with water (140 mL), concentrated and dried in vacuo to give a solid. 300 mL MeOH was added to the solid and the mixture was heated to reflux. Water was added (30 mL) followed by reflux for 5 min. The mixture was slowly allowed to reach r.t. The mixture was stirred overnight at r.t. The solid was filtered off to give the title compound as a single isomer (31 g, 58% yield): $^1$H NMR (500 MHz, CDCl$_3$) ppm 1.38 (m, 2H) 1.52 (m, 2H) 1.77 (td, 2H) 2.16 (m, 2H) 2.98 (s, 2H) 3.28 (m, 1H) 3.40 (s, 3H) 7.35 (d, 1H) 7.70 (dd, 1H) 7.88 (d, 1H); MS (ES+) m/z 309 [M+H]$^+$.

Intermediate 4, Isomer 1

Method C

Borane tert-butylamine complex (820 g, 9.4 mol) dissolved in DCM (3.6 L) was charged to a slurry of 6'-bromospiro[cyclohexane-1,2'-indene]-1',4(3'H)-dione (Intermediate 2, 7.46 kg, at 92% w/w NMR assay, 23.4 mol) in DCM (41 L) at about 0-5° C. over about 40 min. After about 1 h., a solution of NaCl (2.68 kg), water (12.9 L) and 37% hydrochloric acid (2.5 L, 31 mol) was charged. The mixture was warmed to about 15° C. and the phases separated after settling into layers. The DCM phase, containing (1r,4r)-6'-Bromo-4-hydroxyspiro[cyclohexane-1,2'-inden]-1'(3'H)-one (Intermediate 3, isomer 1), was returned to the reactor, together with methyl methanesulfonate (2.59 L, 30.5 mol) and tetrabutylammonium chloride (130 g, 0.47 mol). Aq. 50% NaOH (13 L, 229 mol) was then charged to the vigorously agitated reaction mixture over about 1 h. at about 20° C. After holding for about 16 h., water (19 L) was added and the aq. phase discarded after separation. Solvent (34 L) was distilled off at atmospheric pressure and then more solvent (20 L) was distilled off whilst adding EtOH (20 L) in 5 equal portions. EtOH (14 L) was added and the solution cooled to 25° C. A sample (0.3 L) was taken at 40° C. during the cooling. The sample crystallised spontaneously and was recharged to the reactor at 25° C. After re-heating to about 40° C., water (14 L) was charged over about 20 min. The slurry was cooled to about 20° C. and held for 16 h. before filtering. The solids were washed with a mixture of water (4.8 L) and EtOH (6.4 L) and then dried to give the title compound (containing 4.6% of Isomer 2: (1s,4s)-6'-bromo-4-methoxyspiro[cyclohexane-1,2'-inden]-1'(3'H)-one by HPLC-analysis) (5.57 kg, at 91% NMR assay, 16.4 mol, 70% yield): $^1$H NMR (500 MHz, DMSO-$d_6$) ppm 1.22-1.32 (m, 2H), 1.41-1.48 (m, 2H), 1.56 (td, 2H), 1.99-2.07 (m, 2H), 3.01 (s, 2H), 3.16-3.23 (m, 1H), 3.27 (s, 3H), 7.56 (d, 1H), 7.77 (d, 1H), 7.86 (dd, 1H).

Intermediate 5

(N-(5'-Bromo-4-methoxyspiro[cyclohexane-1,2'-indene]-3'(1'H)-ylidene)-2-methylpropane-2-sulfinamide)

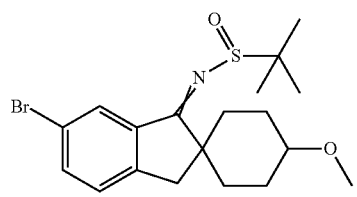 [SMILES: COC1CCC2(CC1)Cc1ccc(Br)cc1C2=NS(=O)C(C)(C)C]

Method A

6'-Bromo-4-methoxyspiro[cyclohexane-1,2'-inden]-1'(3'H)-one (Intermediate 4, mixture of isomers, 1.14 g, 3.69 mmol), 2-methylpropane-2-sulfinamide (0.670 g, 5.53 mmol) and titanium ethoxide (1.519 mL, 7.37 mmol) were dissolved in 2-Me THF (8 mL) and heated to reflux for 26 h. The reaction was left to cool to r.t. EtOAc (80 mL) and NaHCO$_3$ (sat, 15 mL) was added under stirring. The mixture was then left standing without stirring for 15 min. The organic phase was collected by filtration, dried over MgSO$_4$ and concentrated. Flash chromatography with a gradient of 0-20% EtOAc in n-heptane gave the title compound (1.00 g, 66% yield). $^1$H NMR (500 MHz, CD$_3$CN, signals for the major isomer) δ ppm 0.85-0.91 (m, 1H), 1.27 (s, 9H), 1.25-1.86 (multiplets, 5H), 2.01-2.10 (m, 2H), 3.02 (br. s, 2H), 3.18- 3.26 (m, 1H), 3.31 (s, 3H), 7.37 (d, 1H), 7.67 (dd, 1H), 8.59 (br. s., 1H), MS (ES+) m/z 413 [M+H]$^+$.

Intermediate 5, Isomer 1

N-((1r,4r)-5'-Bromo-4-methoxyspiro[cyclohexane-1,2'-indene]-3'(1'H)-ylidene)-2-methylpropane-2-sulfinamide Method B

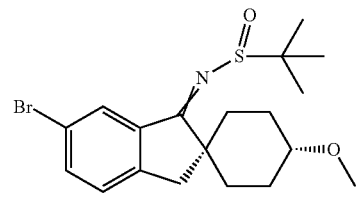 [SMILES: CO[C@H]1CC[C@]2(CC1)Cc1ccc(Br)cc1C2=NS(=O)C(C)(C)C]

(1r,4r)-6'-Bromo-4-methoxyspiro[cyclohexane-1,2'-inden]-1'(3'H)-one (Intermediate 4, isomer 1, method B, 31 g, 100 mmol), 2-methylpropane-2-sulfinamide (15.8 g, 130 mmol), 2-Me THF (200 mL) and titanium ethoxide (41.3 mL, 200 mmol) were heated to 100° C. to give an azeotrope at 74° C. The azeotropic distillation was continued for 8 h and then the mixture was refluxed overnight. The azeotropic distillation was continued for an additional 8 h and then the mixture was refluxed overnight. The mixture was cooled to r.t. Additional 2-Me THF was added to give the original concentration of the mixture. A solution of sulfuric acid (11.14 mL, 200.5 mmol) and Na$_2$SO$_4$ (35.6 g, 250 mmol) in water (150 mL) was prepared. The reaction mixture was then added over 20 min to 4/5 of the volume of the acidic solution. The phases were separated, and the organic phase was washed with the remaining acidic solution, followed by ammonium acetate (15.46 g, 200.5 mmol) in water (75 mL) and water (75 mL). The organic phase was concentrated and dried in vacuo overnight to give the title compound (40.8 g, 99% yield): MS (ES+) m/z 412 [M+H]$^+$.

Intermediate 6

6'-Bromo-4-methoxyspiro[cyclohexane-1,2'-inden]-1'(3'H)-imine

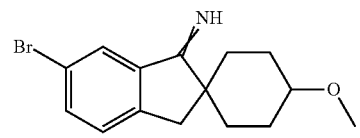 [SMILES: COC1CCC2(CC1)Cc1ccc(Br)cc1C2=N]

Method A

To a solution of N-(5'-bromo-4-methoxyspiro[cyclohexane-1,2'-indene]-3'(1'H)-ylidene)-2-methylpropane-2-sulfinamide (Intermediate 5, mixture of isomers, 2 g, 4.85 mmol) in anhydrous 1,4-dioxane (25 mL) was added 4M HCl in 1,4-dioxane (12.12 mL, 48.50 mmol). A white precipitate was formed immediately and the resulting cloudy mixture was stirred under a nitrogen atmosphere at r.t. for 90 min. Et$_2$O (30 mL) was added and the solid was filtered off and washed with Et₂O. The solid was partitioned between DCM (40 mL) and sat. aq. NaHCO₃ (40 mL). The phases were separated and the organic layer concentrated. The title compound (1.41 g) was used directly in the next step. MS (EI) m/z 307 M⁺.

Method B

Intermediate 6, Isomer 1

(1r,4r)-6'-Bromo-4-methoxyspiro[cyclohexane-1,2'-inden]-1'(3'H)-imine hydrochloride

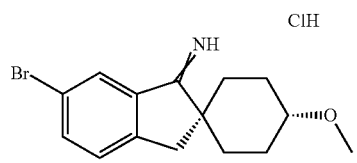 [SMILES: Cl ; CO[C@H]1CC[C@]2(CC1)Cc1ccc(Br)cc1C2=N]

HCl (2 M in Et₂O, 99 mL, 197 mmol) was added dropwise over 5 min to N-((1r,4r)-5'-bromo-4-methoxyspiro[cyclohexane-1,2'-indene]-3'(1'H)-ylidene)-2-methylpropane-2-sulfinamide (Intermediate 5, isomer 1, 40.8 g, 98.9 mmol) dissolved in Et₂O (30 mL) and DCM (30 mL). The mixture was stirred for 60 min before it was filtered. The filter cake was washed with Et₂O and dried in vacuo to give the title compound (31.3 g, 92% yield): ¹H NMR (500 MHz, DMSO-d₆) ppm 1.28 (m, 2H) 1.70 (d, 2H) 2.04 (m, 4H) 3.17 (s, 2H) 3.23 (m, 1H) 3.28 (s, 3H) 7.61 (d, 1H) 8.04 (dd, 1H) 8.81 (s, 1H); MS (EI) m/z 307 M⁺.

Method C

Intermediate 6, Isomer 1

(1r,4r)-6'-Bromo-4-methoxyspiro[cyclohexane-1,2'-inden]-1'(3'H)-one (Intermediate 5, isomer 1, 19.20 g at 91% NMR assay, 56.5 mmol) is reacted with 2-methylpropane-2-sulfinamide (8.90 g, 73.5 mmol) by heating with titanium (IV) ethoxide (24 mL, 115 mmol) and 2-Me THF (44 mL) at about 82° C. Three portions of solvent (about 26 mL per portion) were distilled off after 0.5 h, 7.5 h and 8 h periods of heating respectively, and more 2-Me THF (26 mL per portion, three portions) added after completing each distillation. A further portion of solvent (about 26 mL) was distilled off after 17.5 h. The reaction mixture was cooled to r.t., diluted with DCM (52.5 mL) and then added gradually to a solution (92 mL, 113 g) prepared from Na₂SO₄ (17.9% w/w), water (72.2% w/w) and sulfuric acid (9.9% w/w) over about 4 min. DCM (52.5 mL) was used to wash the reaction flask and addition funnel and then added to the work-up flask. After separating the layers, the organic phase was washed with a mixture of water (17.5 mL) and a solution (18.5 mL, 23 g) prepared from Na₂SO₄ (17.9% w/w), water (72.2% w/w) and sulfuric acid (9.9% w/w). The mixture was stirred with Na₂SO₄ (8.75 g) for about 6 h. The slurry was filtered and the filter cake washed with DCM (17.5 mL). The combined filtrates were concentrated by distilling off the solvent (about 108 mL). Further DCM (52.5 mL) was added and the same volume of solvent (52.5 mL) was distilled off. The dry solution was cooled to about 20° C. and diluted with DCM (17.5 mL) and EtOH (8.7 mL). HCl (2 M in Et₂O) (34 mL, 68 mmol), was then added gradually over about 20 min. The resulting slurry was held at about 20° C. for about 45 min before filtering. The filter cake was washed with a solution (17.5 mL per portion, three portions) prepared from equal volumes of DCM and Et₂O and then dried in vacuo to give the title compound containing about 4% of another isomer (17.41 g at 88% w/w NMR assay, 44.4 mmol, 79% yield) (residual DCM was detected at 6.8% w/w and ammonium chloride 2.9% w/w in the NMR assay): ¹H NMR (500 MHz, DMSO-d₆) ppm 1.30 (m, 2H), 1.70 (d, 2H), 1.98 (m, 2H), 2.10 (m, 2H), 3.17 (s, 2H), 3.23 (m, 1H), 3.29 (s, 3H), 7.61 (d, 1H), 8.04 (dd, 1H), 8.75 (d, 1H), 12.90 (br s, 2H).

Intermediate 7

6'-Bromo-4-methoxy-5''-methyl-3'H-dispiro[cyclohexane-1,2'-indene-1',2''-imidazole]-4''(3''H)-thione

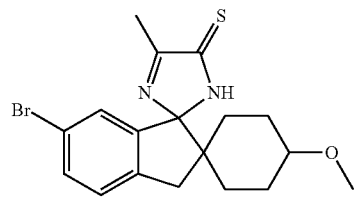 [SMILES: COC1CCC2(CC1)Cc1ccc(Br)cc1C21N=C(C)C(=S)N1]

Method A

6'-Bromo-4-methoxyspiro[cyclohexane-1,2'-inden]-1'(3'H)-imine (Intermediate 6, 1.41 g, 4.57 mmol) and 2-oxopropanethioamide (Intermediate 2, 1.42 g, 13.7 mmol) were dissolved in dry MeOH (30 mL) and the resulting solution was heated at 60° C. under an atmosphere of nitrogen. After 15 h the reaction was allowed to cool to r.t. A precipitate had formed which was filtered off and dried in vacuo, yielding the title compound (1.16 g, 64% yield) as a mixture of isomers. ¹H NMR (500 MHz, DMSO-d₆) δ ppm 1.18 (m, 4H), 1.47 (m, 2H), 1.87 (m, 2H), 2.27 (m, 3H), 3.03 (m, 3H), 3.20 (s, 3H), 6.98 (d, 1H), 7.34 (d, 1H), 7.51 (dd, 1H); MS (APCI+) m/z 394 [M+H]⁺.

Method B

Intermediate 7, Isomer 1

(1r,4r)-6'-Bromo-4-methoxy-5''-methyl-3'H-dispiro[cyclohexane-1,2'-inden-1',2''-imidazole]-4''(3''H)-thione

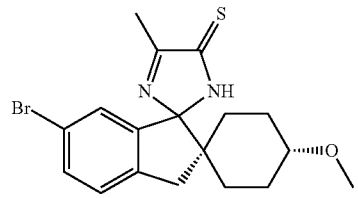

(1r,4r)-6'-Bromo-4-methoxyspiro[cyclohexane-1,2'-inden]-1'(3'H)-imine hydrochloride (Intermediate 6, isomer 1, 95 g, 200 mmol) (containing 30% (1s,4s)-6'-bromo-4-methoxyspiro[cyclohexane-1,2'-inden]-1'(3'H)-imine hydrochloride) was portioned between DCM (600 mL) and 2 M aq. NaOH (400 mL). The organic phase was concentrated and 2-propanol (200 mL) was added and the mixture was concentrated. The resulting (1r,4r)-6'-bromo-4-methoxyspiro[cyclohexane-1,2'-inden]-1'(3'H)-imine, trimethyl orthoformate (66 mL, 602 mmol) and 2-propanol (300 mL) was heated to 80° C. 2-oxopropanethioamide (51.5 g, 500 mmol) in 2-propanol (250 mL) was added during 40 min while keeping the temperature above 65° C. The reaction was stirred at 75° C. for 2 h. The mixture was concentrated to ~½ the volume and was left at 0° C. overnight. A solid was formed that was filtered off, and dried in a vacuum cabinet at 40° C. for 3 h to give the title compound (61.24 g, 78% yield, containing 14% of (1s,4s)-6'-bromo-4-methoxy-5"-methyl-3'H-dispiro[cyclohexane-1,2'-inden-1',2'-imidazole]-4"(3"H)-thione): MS (EI) m/z 392 M Intermediate 8

6'-Bromo-4-methoxy-5"-methyl-3'H-dispiro[cyclohexane-1,2'-indene-1',2"-imidazol]-4"-amine

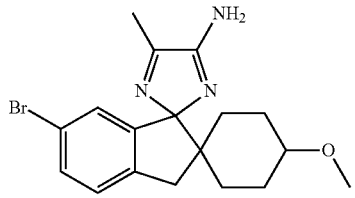 [SMILES: COC1CCC2(CC1)Cc1ccc(Br)cc1C21N=C(C)C(N)=N1]

Method A

6'-Bromo-4-methoxy-5"-methyl-3'H-dispiro[cyclohexane-1,2'-indene-1',2"-imidazole]-4"(3"H)-thione (Intermediate 7, 0.936 g, 2.38 mmol) was taken up in ammonia (7M in MeOH, 10 mL, 70.00 mmol) and the resulting mixture was bubbled with argon and then heated in the MW reactor at 120° C. for 1 h. The solvent was evaporated. Ammonia (7M in MeOH, 6 mL, 42 mmol) was added and the reaction was bubbled with argon and heated again using MW for 60 min at 120° C. The solvent was evaporated and ammonia (7M in MeOH, 10 mL, 70 mmol) was added. The reaction was bubbled with argon and then heated using MW for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 20 mL, 140 mmol) was added. The reaction was heated again using MW for 1 h at 120° C. The solvent was evaporated and the resulting residue was taken up in DCM (60 mL) and brine (×2) and poured into a phase separator. The organic phase was dried with MgSO$_4$, filtered and evaporated to give the title compound (0.736 g, 82% yield) as a mixture of isomers: $^1$H NMR (500 MHz, CDCl$_3$) ppm 1.09 (td, 1H), 1.27-1.49 (m, 3H), 1.62-1.74 (m, 2H), 1.93-2.01 (m, 2H), 2.37 (s, 3H), 3.04-3.18 (m, 3H), 3.34 (s, 3H), 6.90 (d, 1H), 7.20 (d, 1H), 7.38 (dd, 1H); MS (MM-ES+APCI)+m/z 376 [M+H]$^+$.

Separation of the Isomers of 6'-bromo-4-methoxy-5"-methyl-3'H-dispiro[cyclohexane-1,2'-indene-1', 2"-imidazol]-4"-amine 6'-Bromo-4-methoxy-5"-methyl-3'H-dispiro[cyclohexane-1,2'-indene-1',2"-imidazol]-4"-amine (Intermediate 8, 80 mg, 0.21 mmol) was purified using preparative chromatography (Waters FractionLynx system equipped with a XBridge® Prep C8 10 µm OBD™ 19×250 mm column and a guard column; XTerra® Prep MS C8 10 µm 19×10 mm Cartridge. A linear gradient of 35-70% MeOH in 0.2% NH$_3$ in MiiliQ water was applied at flow rate of 20 mL/min) to give:

Isomeric Mixture 1: (1s,4s)-6'-Bromo-4-methoxy-5"-methyl-3'H-dispiro[cyclohexane-1,2'-indene-1',2"-imidazol]-4"-amine (the First to Elute, Minor Isomer, 2.0 mg, 2.5% Yield)

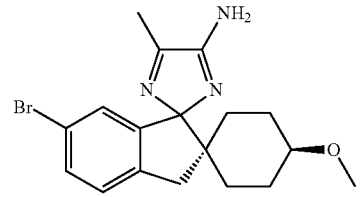

$^1$H NMR (500 MHz, CD$_3$CN) δ ppm 1.15-1.25 (m, 2H), 1.36 (td, 1H), 1.45-1.59 (m, 2H), 1.63-1.74 (m, 3H), 2.19 (s, 3H), 2.98-3.06 (dd, 2H), 3.20 (s, 3H), 3.32 (t, 1H), 5.19-5.39 (m, 2H), 6.75 (d, 1H), 7.20 (d, 1H), 7.34 (dd, 1H); MS (ES+) m/z 378 [M+H]$^+$.

And Isomeric Mixture 2: (1r,4r)-6'-Bromo-4-methoxy-5"-methyl-3'H-dispiro[cyclohexane-1,2'-indene-1',2"-imidazol]-4"-amine (the Second to Elute, Major Isomer, Yield not Determined)

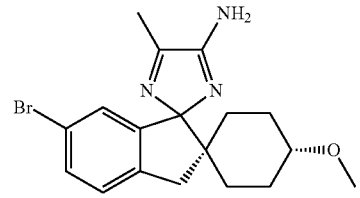

$^1$H NMR (500 MHz, CDCl$_3$) δ ppm 1.09 (td, 3.47 Hz, 1H), 1.27-1.49 (m, 3H), 1.62-1.74 (m, 2H), 1.93-2.01 (m, 2H), 2.37 (s, 3H), 3.04-3.18 (m, 3H), 3.34 (s, 3H), 6.90 (d, 1H), 7.20 (d1H), 7.38 (dd, 1.73 Hz, 1H), MS (MM-ES+APCI)+ m/z 378 [M+H]$^+$.

Separation of the Isomers of (1r,4r)-6'-bromo-4-methoxy-5"-methyl-3'H-dispiro-[cyclohexane-1,2'-indene-1',2"-imidazol]-4"-amine The isomers of Isomeric mixture 2 of Intermediate 8 were separated using SFC Berger Multigram II, with a LuxC4;

4.6*250 mm; 5 µm column, and a mobile phase consisting of 15% MeOH (containing 0.1% DEA) and 85% $CO_2$ at a flow rate of 50 mL/min to give:

Isomer 1: (1r,1'R,4R)-6'-Bromo-4-methoxy-5"-methyl-3'H-dispiro[cyclohexane-1,2'-indene-1',2"-imidazol]-4"-amine (9 mg, 11% yield) with Retention Time 6.1 Min

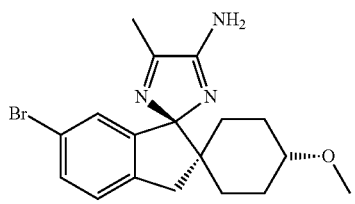

$^1$H NMR (500 MHz, $CD_3CN$) δ ppm 1.05 (dd, 1H), 1.23 (dt, 2H), 1.39 (d, 1H), 1.49 (ddd, 2H), 1.81-1.89 (m, 2H), 2.17 (s, 3H), 2.94-3.10 (m, 3H), 3.23 (s, 3H), 5.32 (br. s., 2H), 6.75 (d, 1H), 7.19 (d, 1H), 7.33 (dd, 1H), MS (MM-ES+APCI)+ m/z 378 [M+H]$^+$;

And Isomer 2: (1r,1'S,4S)-6'-Bromo-4-methoxy-5"-methyl-3'H-dispiro[cyclohexane-1,2'-indene-1',2"-imidazol]-4"-amine (15 mg, 19% yield) with Retention Time 9.5 Min

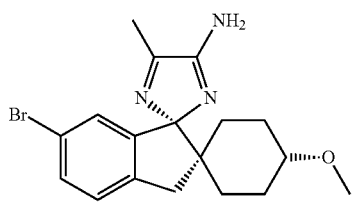

$^1$H NMR (500 MHz, $CD_3CN$) δ ppm 1.00-1.09 (m, 1H), 1.17-1.31 (m, 2H), 1.39 (td, 1H), 1.50 (ddd, 2H), 1.86 (dt, 2H), 2.18 (s, 3H), 2.94-3.10 (m, 3H), 3.24 (s, 3H), 5.32 (br. s., 2H), 6.76 (d, 1H), 7.20 (d, 1H), 7.34 (dd, 1H), MS (MM-ES+APCI)+ m/z 378 [M+H]$^+$.

Separation of the Isomers of (1s,4s)-6'-bromo-4-methoxy-5"-methyl-3'H-dispiro-[cyclohexane-1,2'-indene-1',2"-imidazol]-4"-amine 1.7 g of a mixture containing (1r,4r)-6'-bromo-4-methoxy-5"-methyl-3'H-dispiro[cyclohexane-1,2'-indene-1',2"-imidazol]-4"-amine (Intermediate 8, isomeric mixture 2, major) and (1s,4s)-6'-bromo-4-methoxy-5"-methyl-3'H-dispiro[cyclohexane-1,2'-indene-1',2"-imidazol]-4"-amine (Intermediate 8, isomeric mixture 1, minor) was purified by preparative chromatography using the following conditions: Column: XBridge C18; 50*300 mm; 10 µm, Mobile phase: 20-60% MeCN in 0.1% aq. $NH_3$ over 20 min, Flow rate: 120 mL/min. The obtained minor isomer (equivalent to Isomeric mixture 1 above) with retention time 15 min, was then separated into its isomers by preparative SFC using the following system: Berger Multigram II SFC system, Column: Chiralcel OD-H; 20*250 mm; 5 µm, Mobile phase: 10% MeOH (containing 0.1% DEA)/90% $CO_2$, Flow rate: 50 mL/min resulting in:

Isomer 3 with undetermined absolute configuration (77 mg, 5% yield) with retention time 6.5 min: $^1$H NMR (400 MHz, DMSO-$d_6$) δ ppm 1.05-1.17 (m, 2H), 1.24 (td, 1H), 1.36-1.54 (m, 2H), 1.57-1.74 (m, 3H), 2.16 (s, 3H), 2.85-3.07 (m, 2H), 3.12 (s, 3H), 3.29 (br. s., 1H), 6.58 (s, 2H), 6.63 (d, 1H), 7.24 (d, 1H), 7.33 (dd, 1H); MS (APCI$^+$) m/z 376 [M+H]$^+$, and Isomer 4 with undetermined absolute configuration (64 mg, 4% yield) with retention time 12 min: $^1$H NMR (400 MHz, DMSO-$d_6$) δ ppm 1.05-1.17 (m, 2H), 1.24 (td, 1H), 1.36-1.55 (m, 2H), 1.57-1.74 (m, 3H), 2.16 (s, 3H), 2.85-3.06 (m, 2H), 3.12 (s, 3H), 3.29 (br. s., 1H), 6.58 (s, 2H), 6.63 (d, 1H), 7.24 (d, 1H), 7.33 (dd, 1H); MS (APCI$^+$) m/z 376 [M+H]$^+$.

Method B

Intermediate 8, Isomeric Mixture 2

(1r,4r)-6'-Bromo-4-methoxy-5"-methyl-3'H-dispiro [cyclohexane-1,2'-indene-1',2"-imidazol]-4"-amine

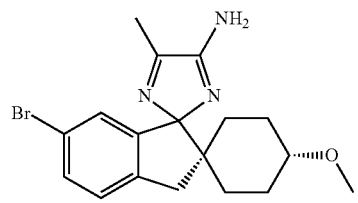

(1r,4r)-6'-Bromo-4-methoxy-5"-methyl-3'H-dispiro[cyclohexane-1,2'-indene-1',2"-imidazole]-4"(3"H)-thione (Intermediate 7, isomer 1, 22.7 g, 57.7 mmol) and ammonia (7 M in MeOH, 180 mL, 1.26 mol) was put in a pressure reactor and heated to 74° C. overnight. The residue was allowed to reach r.t. and the mixture was concentrated. The residue was partitioned between 2 M citric acid (400 mL) and EtOAc (400 mL). Insoluble material was filtered off and was determined to be unreacted starting material. The organic phase (org 1) was concentrated in vacuo to give additional unreacted starting material. To the aqueous phase was EtOAc (300 mL) added and then 50% NaOH was added until pH~12, and the mixture was stirred for 10 min. The resulting organic phase (org 2) was saved. The residue from org 1, and the solid filtered off were combined and suspended in ammonia (7 M in MeOH, 180 mL, 1.26 mmol) and put in a pressure reactor and heated 100° C. overnight. The obtained solution was concentrated in vacuo. The residue was partitioned between 2 M citric acid (300 mL) and EtOAc (300 mL). To the aqueous phase was EtOAc (300 mL) added and then 50% NaOH was added until pH~12, and the mixture was stirred for 10 min. The organic phase was combined with org 2 from above. Activated charcoal was added to the organic phase and the mixture was stirred for 30 min before it was filtered through diatomaceous earth. The organic phase was concentrated and dried in vacuo overnight to give a solid. To the solid was diisopropyl ether (125 mL) added and the mixture was refluxed overnight. The mixture was allowed to reach r.t. and the solid was filtered off to give the title compound (equivalent to Intermediate 8, isomeric mixture 2 above) (15 g, 69% yield): $^1$H NMR (500 MHz, DMSO-$d_6$) ppm 0.93 (m, 1H) 1.1-1.25 (m, 2H) 1.35-1.45 (m, 3H) 1.81 (br. d, 2H) 2.16 (s, 3H) 2.87-3.03 (m, 3H) 3.18 (s, 3H) 6.59 (br. s., 2H), 6.64 (d, 1H), 7.25 (d, 1H), 7.34 (dd, 1H); ES+) m/z 376 [M+H]+.

Intermediate 8, Isomer 1

(1r,1'R,4R)-6'-Bromo-4-methoxy-5''methyl-3'H-dispiro[cyclohexane-1',2''-indene-1',2''imidazol]-4''-amine

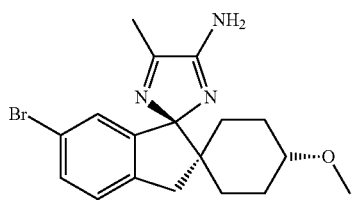

To a 1 L round-bottomed flask was added (1r,4r)-6'-bromo-4-methoxy-5''-methyl-3'H-dispiro[cyclohexane-1,2'-indene-1',2''-imidazol]-4''-amine (Intermediate 8, isomeric mixture 2, Method B, 61 g, 162 mmol), EtOH (99.5%, 600 mL) and water (60 mL) to give a homogeneous mixture which was heated to 70° C. The mixture was stirred for 30 min at the elevated temperature followed by addition of D(+)-10-camphorsulfonic acid (18.8 g, 81.0 mmol). The mixture was stirred at 70° C. for 3 h and then allowed to reach 20° C. over 2 h followed by stirring at 20° C. for 12 h. The mixture was filtered to give a solid that was washed with cold EtOH and then dried in a vacuum oven at 50° C. for 10 h to give the title compound as a D(+)-10-camphorsulfonic salt (37 g; 37% yield). Enantiomeric ratio was determined by analysis on a SFC Berger Analytix system equipped with a Chiralpak AD-H column (4.6*250 mm; 5 µm) and a mobile phase consisting of 10% MeOH (containing 0.1% DEA) and 90% CO$_2$ at a flow rate of 3 mL/min. The first peak with retention time 3.68 min (area 2.5%) corresponded to (1r,1'S,4S)-6'-bromo-4-methoxy-5''-methyl-3'H-dispiro[cyclohexane-1,2'-indene-1',2''-imidazol]-4''-amine, equivalent to Isomer 2. The second peak with retention time 4.58 min (area 97.5%) corresponded to the title compound (1r,1'R,4R)-6'-bromo-4-methoxy-5''methyl-3'H-dispiro[cyclohexane-1',2''-indene-1',2''imidazol]-4''-amine, equivalent to Isomer 1.

The liberation of the title compound from the salt was carried out by stirring the camphorsulfonic acid salt (0.32 g, 0.53 mmol) suspended in dichloromethane (4 mL) with an aqueous solution (4 mL) of KOH (0.32 g, 5.7 mmol) at r.t. during 30 min. The organic phase was separated and concentrated in vacuo to give title compound quantitatively with an enantiomeric excess of 95% (determined as above).

Method C

Intermediate 8, Isomer 1 (+)-Camphor Sulfonylate (1r,1'R,4R)-6'-Bromo-4-methoxy-5''methyl-3'H-dispiro[cyclohexane-1',2''-indene-1',2''imidazol]-4''-amine (+)-camphor sulfonylate (1r,4r)-6'-Bromo-4-methoxy-5''-methyl-3'H-dispiro[cyclohexane-1,2'-indene-1',2''-imidazole]-4''(3''H)-thione (Intermediate 7, isomer 1, 12.8 g, 32.6 mmol), ammonia (7 M in MeOH, 93.3 mL, 653 mmol) and zinc acetate dihydrate (8.60 g, 39.2 mmol) were charged to a pressure reactor and heated to 80° C. for 24 h. The reaction mixture was cooled down. and the solvent changed into 1-butanol, final volume 130 mL (1-BuOH (130 mL) was added, then the mixture was distilled down to 130 mL, at which stage distillation was continued while additional 1-BuOH (65 mL) was added to maintain the volume). The organic solution was washed with 1 M aq. sodium hydroxide solution (85 mL) and water (51 mL). The resultant solution was heated to 70° C. and D(+)-10-camphorsulfonic acid (6.82 g, 29.4 mmol) added. The mixture was cooled and the resulting solid collected by filtration, washed with ethanol (51 mL) and dried in a vacuum oven at 40° C. affording the title compound as a white solid (7.09 g, 41% yield) with 99% enantiomeric purity (chromatography: ChiralPak IA-3 0.46 cm×5 cm, column temperature 20° C. with a mobile phase consisting of 95:5 isohexane:ethanol (0.1% v/v triethylamine) at a flow rate of 0.9 mL/min, Intermediate 8, isomer 1: retention time 2.66 min, Intermediate 8, isomer 2 retention time 2.39 min).

Intermediate 9

Di-tert-butyl [(1r,4r)-6'-bromo-4-methoxy-5''-methyl-3'H-dispiro[cyclohexane-1,2'-indene-1',2''-imidazol]-4''-yl]imidodicarbonate

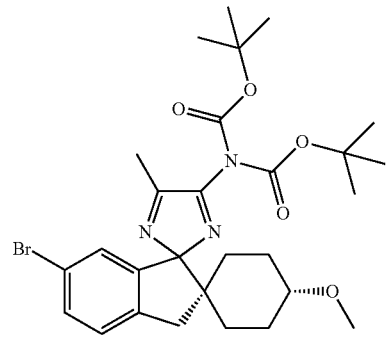

Di-tert-butyl dicarbonate (8.53 g, 39.1 mmol), Et$_3$N (5.44 mL, 39.1 mmol) and DMAP (0.227 g, 1.86 mmol) were added to a solution of (1r,4r)-6'-bromo-4-methoxy-5''-methyl-3'H-dispiro[cyclohexane-1,2'-indene-1',2''-imidazol]-4''-amine (Intermediate 8, isomeric mixture 2, 7.00 g, 18.6 mmol) in DCM (100 mL). The resulting mixture was stirred at r.t. for 20 h. The reaction mixture was diluted with DCM and washed with 2 M aqueous HCl, water, aq. sat. NaHCO$_3$ and brine, dried over MgSO$_4$ and concentrated. Purification by chromatography on silica using gradient elution of 0-5% methanol in DCM gave the title compound (4.41 g, 41% yield). $^1$H NMR (500 MHz, DMSO-d$_6$) ppm 1.1-1.3 (m, 4H), 1.4 (s, 18H), 1.5-1.6 (m, 2H), 1.8-1.9 (m, 2H), 2.2 (s, 3H), 2.9-3.0 (m, 1H), 3.1 (s, 2H), 3.2 (s, 3H), 6.7 (d, 1H), 7.4 (d, 1H), 7.5 (dd, 1H). MS (ES+) m/z 576 [M+H]+.

Intermediate 10 tert-Butyl [(1r,4r)-6'-bromo-4-methoxy-5"-methyl-3'H-dispiro[cyclohexane-1,2'-indene-1',2"-imidazol]-4"-yl]carbamate

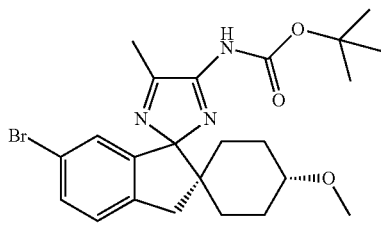

A mixture of di-tert-butyl [(1r,4r)-6'-bromo-4-methoxy-5"-methyl-3'H-dispiro[cyclohexane-1,2'-indene-1',2"-imidazol]-4"-yl]imidodicarbonate and t-butyl [(1r,4r)-6'-bromo-4-methoxy-5"-methyl-3'H-dispiro[cyclohexane-1,2'-indene-1',2"-imidazol]-4"-yl]imidocarbonate (Intermediate 9, used as mixture not subjected to chromatography, 4.09 g, 7.78 mmol) was treated with 2 M aqueous $Na_2CO_3$ (7.1 mL, 14 mmol) at 40° C. for 8 h. Most of the methanol was evaporated at reduced pressure and the residue was extracted with EtOAc. The combined extracts were washed with brine, dried over $MgSO_4$ and concentrated. Purification by chromatography on silica using gradient elution of 0-10% MeOH in a mixture of DCM and heptane (15:85) gave a product displaying a $^1$H NMR consistent with a 1:1 mixture of two isomers of the title compound (2.90 g, 86% yield). $^1$H NMR (500 MHz, DMSO-$d_6$) δ ppm 1.44 (s partially overlapped with multiplet, 9H), 1.47 (s partially overlapped with multiplet, 9H), 2.18 (s, 3H), 2.28 (s, 3H), 3.18 (s partially overlapped with multiplet, 4H), 3.20 (s partially overlapped with multiplet, 3H), 6.66 (d, 1H), 7.03 (m, 1H), 7.31 (m, 2H), 7.41 (dd, 1H), 7.48 (dd, 1H), 9.85 (s, 1H), 10.52 (s, 1H); MS (ES+) m/z 476 $[M+H]^+$.

Intermediate 11

6-((3,3-Difluorocyclobutyl)methoxy)-2,3-dihydro-1H-inden-1-one

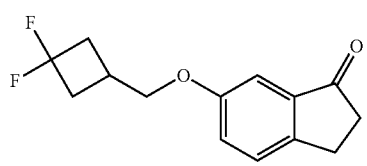 [SMILES: O=C1CCc2ccc(OCC3CC(F)(F)C3)cc21]

To a solution of 6-hydroxy-2,3-dihydro-1H-inden-1-one (3.6 g, 24.3 mmol) in THF (60 mL) were (3,3-difluorocyclobutyl)methanol (2.97 g, 24.3 mmol) and triphenylphosphine (9.56 g, 36.45 mmol) added. Diisopropyl azodicarboxylate (7.18 mL, 36.5 mmol) was added dropwise. The reaction mixture was stirred at r.t. overnight. The material was purified by flash column chromatography using a gradient of 0-100% EtOAc in heptane, providing 3.67 g (60% yield) of the title compound. $^1$H NMR (500 MHz, DMSO-$d_6$) ppm 2.30 (br. s., 1H) 2.42-2.52 (m, 6H) 2.54-2.62 (m, 1H) 2.63-2.66 (m, 2H) 2.67-2.76 (m, 2H) 2.98-3.04 (m, 2H) 4.08 (d, 2H) 7.10 (d, 1H) 7.26 (dd, 1H) 7.48 (d, 1H); MS (ES+) m/z 253 $[M+H]^+$.

Intermediate 12

6'-((3,3-Difluorocyclobutyl)methoxy)spiro[cyclohexane-1,2'-indene]-1',4(3'H)-dione

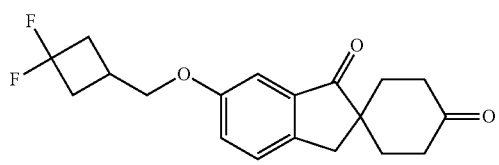 [SMILES: O=C1CCC2(CC1)Cc1ccc(OCC3CC(F)(F)C3)cc1C2=O]

A mixture of 6-((3,3-difluorocyclobutyl)methoxy)-2,3-dihydro-1H-inden-1-one (Intermediate 11, 7.0 g, 27.8 mmol) and methyl acrylate (5.51 mL, 61.1 mmol) in 2-Me THF (6 mL) was cooled to 0° C. and potassium tert-butoxide (3.74 g, 33.3 mmol) was added in portions. After stirring for 2 h at r.t., water (9 mL) and potassium hydroxide (1.56 g, 27.8 mmol) were added and the mixture was heated at reflux overnight. The mixture was cooled to r.t. and water and brine was added. The layers were separated and the aqueous layer extracted with EtOAc. The combined organic layers were dried over $MgSO_4$ and concentrated, providing 3.51 g, 37% yield of the title compound. $^1$H NMR (500 MHz, $CDCl_3$) ppm 1.80-1.91 (m, 2H) 2.17-2.26 (m, 2H) 2.39-2.57 (m, 4H) 2.58-2.82 (m, 5H) 3.16 (s, 2H) 4.05 (d, 2H) 7.20 (d, 1H) 7.25 (dd, 1H) 7.40 (d, 1H); MS (ES+) m/z 335 $[M+H]^+$.

Intermediate 13

6'-((3,3-Difluorocyclobutyl)methoxy)-4-hydroxyspiro[cyclohexane-1,2'-inden]-1'(3'H)-one

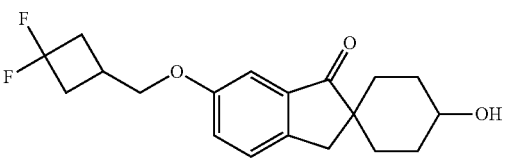 [SMILES: O=C1c2cc(OCC3CC(F)(F)C3)ccc2CC12CCC(O)CC2]

6'-((3,3-Difluorocyclobutyl)methoxy)spiro[cyclohexane-1,2'-indene]-1',4(3'H)-dione (Intermediate 12, 3.51 g, 10.5 mmol) were dissolved in the mixture of THF (50 mL) and methanol (4.25 mL, 105 mmol). Borane-trimethylamine complex (1.69 g, 23.1 mmol) was added and the mixture was stirred overnight. Citric acid monohydrate (30.9 g, 147 mmol) was added in one portion, followed by dropwise addition of water (3.78 mL, 210 mmol). The mixture was stirred for 3 h before being diluted with water and extracted with EtOAc (×2). The combined organic phases were dried and concentrated. The product was purified using column chro-

Intermediate 14

6'-((3,3-Difluorocyclobutyl)methoxy)-4-methoxyspiro[cyclohexane-1,2'-inden]-1'(3'H)-one

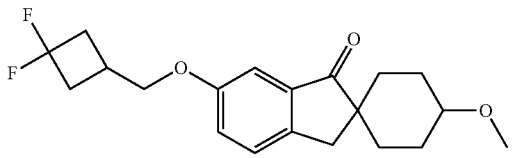 [SMILES: COC1CCC2(CC1)Cc1ccc(OCC3CC(F)(F)C3)cc1C2=O]

6'-((3,3-difluorocyclobutyl)methoxy)-4-hydroxyspiro[cyclohexane-1,2'-inden]-1' (3'H)-one (Intermediate 13, 2.98 g, 8.85 mmol) was dissolved in THF (35 mL) under an atmosphere of nitrogen, and the solution was cooled to 0° C. Potassium tert-butoxide (2.98 g, 26.6 mmol) was added portionwise and the mixture was stirred at 0° C. for 15 min. Methyl iodide (1.11 mL, 17.7 mmol) was added. The cooling bath was removed, and the mixture was stirred at r.t. overnight. Water (200 mL) was added and the resulting solution was partitioned between additional water (200 mL) and EtOAc (400 mL). The organic phases was dried (MgSO₄) and concentrated, and the product was isolated using column chromatography (0-50% EtOAc in heptane) providing 1.85 g (59% yield) of the title compound. MS (ES+) m/z 351 [M+H]⁺.

Intermediate 15

6'-(Cyclobutylmethoxy)spiro[cyclohexane-1,2'-indene]-1',4(3'H)-dione

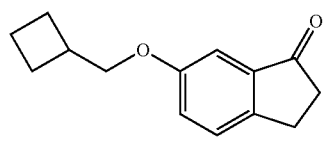 [SMILES: O=C1CCc2ccc(OCC3CCC3)cc21]

The title compound (2.56 g, 58% yield) was prepared using the procedure described for Intermediate 11, starting from 6-hydroxy-2,3-dihydro-1H-inden-1-one (3.0 g, 20.3 mmol) and cyclobutylmethanol (2.10 mL, 22.3 mmol). The mixture was heated to 45° C. and left stirring over a weekend. ¹H NMR (500 MHz, CDCl₃) δ ppm 1.81-2.03 (m, 4H), 2.11-2.20 (m, 2H), 2.69-2.74 (m, 2H), 2.78 (dt, 1H), 3.04-3.12 (m, 2H), 3.96 (d, 2H), 7.17-7.22 (m, 2H), 7.36 (d, 1H); MS (ES+) m/z 217 [M+H]⁺.

Intermediate 16

(1r,4r)-6'-(Cyclobutylmethoxy)-4-hydroxyspiro[cyclohexane-1,2'-inden]-1'(3'H)-one

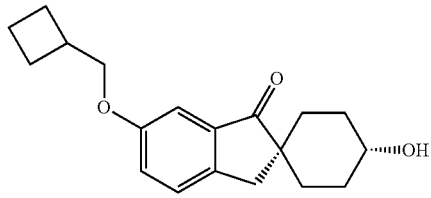 [SMILES: O=C1c2cc(OCC3CCC3)ccc2C[C@]12CC[C@@H](O)CC2]

The title compound was prepared using the procedure described for Intermediate 13, starting from 6'-(cyclobutylmethoxy)spiro[cyclohexane-1,2'-indene]-1',4(3'H)-dione (Intermediate 15, 2.35 g, 7.88 mmol) The product was purified on a silica gel column (gradient elution 0-50% EtOAc in n-heptane) to give the title compound (1.84 g, 78% yield, containing 29% of (1s,4s)-6'-(cyclobutylmethoxy)-4-hydroxyspiro[cyclohexane-1,2'-inden]-1'(3'H)-one). The compound was used in the next step: ¹H NMR (500 MHz, DMSO-d₆) δ ppm 1.10 (m, minor isomer), 1.2-1.4 (m, 4H), 1.57 (m, 2H), 1.71 (m, minor isomer), 1.75-1.95 (m, 6H), 2.07 (m, 2H), 2.71 (m, 1H), 2.92 (m, 2H), 3.44 (m, 1H), 3.84 (m, minor isomer), 3.98 (d, 2H), 4.42 (d, minor isomer), 4.66 (d, 1H), 7.07 (d, 1H), 7.26 (m, 1H), 7.44 (m, 1H); MS (ES+) m/z 301.1 [M+H]⁺.

Intermediate 17

(1r,4r)-6'-(Cyclobutylmethoxy)-4-methoxyspiro[cyclohexane-1,2'-inden]-1'(3'H)-one

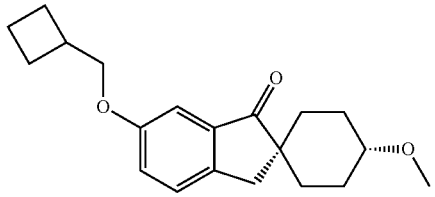 [SMILES: CO[C@H]1CC[C@]2(CC1)Cc1ccc(OCC3CCC3)cc1C2=O]

(1r,4r)-6'-(Cyclobutylmethoxy)-4-hydroxyspiro[cyclohexane-1,2'-inden]-1'(3'H)-one (Intermediate 16, containing 29% of another isomer, 1.84 g, 6.13 mmol) was dissolved in 2-Me THF (17 mL) under an inert atmosphere and the solution was cooled to 0° C. Methyl iodide (0.498 mL, 7.96 mmol) was added followed by portionwise addition of potassium tert-butoxide (0.962 g, 8.58 mmol). The resulting mixture was stirred at 35° C. for 1 h. Potassium tert-butoxide (0.962 g, 8.58 mmol) was added and stirring continued. After another 30 min, a new portion of potassium tert-butoxide (0.103 g, 0.92 mmol) was added and stirring continued. After a total of 4 h, full conversion was obtained. Water (6 mL) and brine (3 mL) was added. The phases were separated and the organic layer was dried and concentrated. The product was purified on a silica gel column (gradient elution of 0-50%

EtOAc in n-heptane) to give the title compound (1.48 g, 77% yield). The product contained 29% of (1s,4s)-6'-(cyclobutylmethoxy)-4-methoxyspiro[cyclohexane-1,2'-inden]-1'(3'H)-one and was used in next step: $^1$H NMR (500 MHz, DMSO-d$_6$) δ ppm 1.11 (m, minor isomer), 1.26 (m, 2H), 1.40 (d, 1H), 1.57 (m, 2H), 1.75-1.95 (m, 5H), 2.0-2.1 (m, 3H), 2.71 (m, 1H), 2.95 (s, 3H), 2.95 (s, minor isomer), 3.19 (m, 1H), 3.24 (s, minor isomer), 3.26 (s, 3H), 3.45 (m, minor isomer), 3.99 (d, 2H), 7.07 (d, 1H), 7.26 (m, 1H), 7.45 (m, 1H); MS (ES+) m/z 315.1 [M+H]$^+$.

Intermediate 18

N-(5'-((3,3-Difluorocyclobutyl)methoxy)-4-methoxyspiro[cyclohexane-1,2'-inden]-3'(1'H)-ylidene)-2-methylpropane-2-sulfinamide

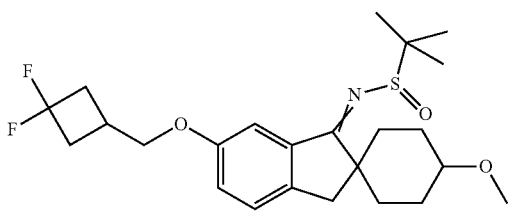 [SMILES: COC1CCC2(CC1)Cc1ccc(OCC3CC(F)(F)C3)cc1C2=NS(=O)C(C)(C)C]

6'-((3,3-Difluorocyclobutyl)methoxy)-4-methoxyspiro[cyclohexane-1,2'-inden]-1'(3'H)-one (Intermediate 14, 1.85 g, 5.28 mmol) and 2-methylpropane-2-sulfinamide (1.15 g, 9.50 mmol) were dissolved in 2-Me THF (40 mL). Tetraethoxytitanium (2.21 mL, 10.6 mmol) was added and the resulting mixture was heated to 80° C. over a weekend. The reaction mixture was cooled to r.t., and diluted with ethyl acetate (85 mL). Water (3 mL) was added under vigorous stirring and then the mixture was allowed to stand for 1 h. The mixture was filtered, the solvent was evaporated and the residue was purified by column chromatography on silica using a gradient of 0-70% ethyl acetate in heptanes. The product was recrystallized twice from EtOH. to give 0.750 g of the title compound (31% yield). MS (ES+) m/z 454 [M+H]$^+$.

Intermediate 19

6'-[(3,3-Difluorocyclobutyl)methoxy]-4-methoxy-5"-methyl-3'H-dispiro[cyclohexane-1,2'-indene-1',2"-imidazole]-4"(3"H)-thione

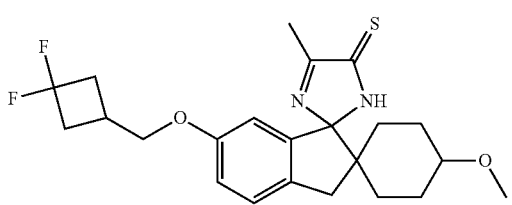 [SMILES: COC1CCC2(CC1)Cc1ccc(OCC3CC(F)(F)C3)cc1C21N=C(C)C(=S)N1]

HCl (4 M in 1,4-dioxane, 4.13 mL, 16.5 mmol) was added to a solution of N-(5'-((3,3-difluorocyclobutyl)methoxy)-4-methoxyspiro[cyclohexane-1,2'-inden]-3'(1'H)-ylidene)-2-methylpropane-2-sulfinamide (Intermediate 18, 750 mg, 1.65 mmol) in anhydrous 1,4-dioxane (25 mL). A white precipitate formed immediately and the resulting cloudy mixture was stirred under a nitrogen atmosphere overnight. The mixture was diluted with NaHCO$_3$ (aq.) and extracted with DCM. The organic phase was dried and concentrated, to yield 6'-((3,3-difluorocyclobutyl)methoxy)-4-methoxyspiro[cyclohexane-1,2'-inden]-1'(3'H)-imine (672 mg, 1.92 mmol). The imine, trimethyl orthoformate (0.557 mL, 5.08 mmol) and 2-propanol (5 mL) was placed into a MW tube and the mixture was heated at 60° C. in an oil bath. 2-oxopropanethioamide (Intermediate 1, 397 mg, 3.85 mmol) in MeOH (15 mL) was added and the resulting mixture was stirred overnight. The mixture was concentrated in vacuo. The product was isolated using column chromatography (0-50% EtOAc in heptane) to give 106 mg (12% yield) of the title compound. MS (ES+) m/z 435 [M+H]$^+$.

Intermediate 20

N-((1r,4r)-5'-(Cyclobutylmethoxy)-4-methoxyspiro[cyclohexane-1,2'-inden]-3'(1'H)-ylidene)-2-methylpropane-2-sulfinamide

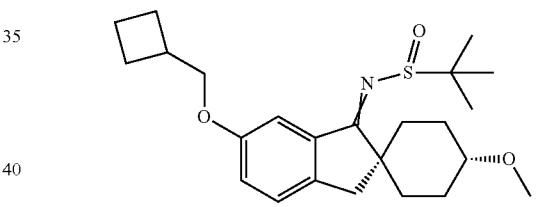

(1r,4r)-6'-(Cyclobutylmethoxy)-4-methoxyspiro[cyclohexane-1,2'-inden]-1'(3'H)-one (Intermediate 17, 1.48 g, 4.71 mmol) and 2-methylpropane-2-sulfinamide (1.027 g, 8.47 mmol) were dissolved in 2-Me THF (17 mL). Titanium(IV) ethoxide (1.97 mL, 9.41 mmol) was added. The resulting mixture was heated to reflux overnight. 2-Methylpropane-2-sulfinamide (0.560 g, 4.62 mmol) was added and the reaction was refluxed for 6 h. Additional 2-methylpropane-2-sulfinamide (0.560 g, 4.62 mmol) and titanium(IV) ethoxide (1 mL, 4.79 mmol) were added and the mixture was refluxed overnight. Additional 2-methylpropane-2-sulfinamide (0.560 g, 4.62 mmol) and titanium(IV) ethoxide (1 mL, 4.79 mmol) were added and the mixture was refluxed overnight (80% conversion). EtOAc (10 mL) and sat. aq. NaHCO$_3$ (2 mL) were added under stirring. The mixture was left to stand still for 1 h. The organic phase was collected by filtration through diatomaceous earth, dried over MgSO$_4$ and concentrated. The product was purified on a silica gel column (gradient elution 0-100% EtOAc in n-heptane) to give the title compound (1.12 g, 57% yield) containing 30% of the (1s,4s)-isomer. It was used in the next step: $^1$H NMR (500 MHz, DMSO-d$_6$) δ ppm 1.26 (m, 11H), 1.50 (m, 3H), 1.87 (m, 5H), 2.06 (m, 4H), 2.73

(m, 1H), 2.96 (m, 2H), 3.17 (m, 1H), 3.26 (s, 3H), 3.95 (d, 2H), 7.22 (m, 1H), 7.40 (m, 1H), 7.83 (m, 1H); MS (ES+) m/z 418.2 [M+H]+.

Intermediate 21

(1r,4r)-6'-(Cyclobutylmethoxy)-4-methoxyspiro[cyclohexane-1,2'-inden]-1'(3'H)-imine

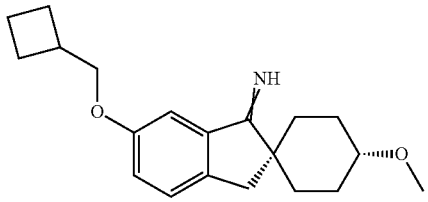 [SMILES: CO[C@H]1CC[C@]2(CC1)Cc1ccc(OCC3CCC3)cc1C2=N]

HCl (4 M in 1,4-dioxane) (6.70 mL, 26.8 mmol) was added to a solution of N-((1r,4r)-5'-(cyclobutylmethoxy)-4-methoxyspiro[cyclohexane-1,2'-indene]-3'(1'H)-ylidene)-2-methylpropane-2-sulfinamide (Intermediate 20, 1.12 g, 2.68 mmol) in anhydrous 1,4-dioxane (8 mL). The reaction mixture was stirred under a nitrogen atmosphere at r.t. for 90 min. DCM (20 mL) and sat aq. NaHCO3 (15 mL) were added to the reaction mixture. The phases were separated and the organic layer concentrated to give the title compound (0.840 g, quantitative yield), that was used directly in next step: MS (ES+) m/z 314.15 [M+H]+.

Intermediate 22

(1r,4r)-6'-(Cyclobutylmethoxy)-4-methoxy-5''-methyl-3'H-dispiro[cyclohexane-1,2'-indene-1',2''-imidazole]-4''(3''H)-thione

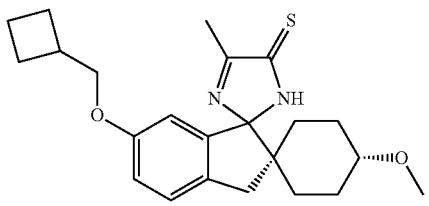

(1r,4r)-6'-(Cyclobutylmethoxy)-4-methoxyspiro[cyclohexane-1,2'-inden]-1'(3'H)-imine (Intermediate 21, 0.84 g, 2.68 mmol) and 2-oxopropanethioamide (Intermediate 1, 0.829 g, 8.04 mmol) were dissolved in dry MeOH (12 mL) and the resulting orange solution was heated at 60° C. under N2 (g) overnight. Additional 2-oxopropanethioamide (0.829 g, 8.04 mmol) was added to the reaction mixture and it was heated to 60° C. for 6 h. The reaction mixture was concentrated and the solvent was changed to 2-propanol (12 mL). Trimethyl orthoformate (0.880 mL, 8.04 mmol) was added. The reaction mixture was heated to 80° C. for about 2 days (20% conversion). The mixture was concentrated. The residue was dissolved in EtOAc and then washed with water. The organic phase was concentrated and the residue was purified on a silica gel column (0-100% EtOAc in n-heptane) to give the title compound (0.140 g, 13% yield). The product contained 15% of the (1s,4s)-isomer and was used in the next step: 1H NMR (500 MHz, DMSO-d6) δ ppm 1.09 (m, 1H) 1.24 (m, 3H) 1.49 (m, 2H) 1.85 (m, 6H) 2.03 (m, 2H) 2.26 (s, 3H) 2.64 (dt, 1H) 2.97 (m, 3H) 3.20 (s, 3H) 3.85 (m, 2H) 6.30 (d, 1H) 6.87 (dd, 1H) 7.23 (d, 1H) 12.29 (s, 1H); MS (ES+) m/z 399.1 [M+H]+.

EXAMPLES

Example 1

(1r,4r)-4-Methoxy-5''-methyl-6'-[(1-methylcyclopropyl)methoxy]-3'H-dispiro[cyclohexane-1,2'-indene-1',2''-imidazol]-4''-amine

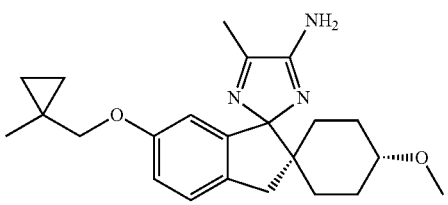

tert-Butyl [(1r,4r)-6'-bromo-4-methoxy-5''-methyl-3'H-dispiro[cyclohexane-1,2'-indene-1',2''-imidazol]-4''-yl]carbamate (Intermediate 10, 315 mg, 0.66 mmol), allylpalladium(II) chloride (5 mg, 0.01 mmol), di-tert-butyl(2',4',6'-triisopropyl-3-methoxy-6-methylbiphenyl-2-yl)phosphine (19 mg, 0.04 mmol) and Cs2CO3 (323 mg, 0.99 mmol) were weighed into a tube. The tube was capped. Toluene (5 mL) was added and the headspace was evacuated and refilled with argon. (1-Methylcyclopropyl)methanol (114 mg, 1.32 mmol) was added and the mixture was heated to 90° C. for 16 h. The cooled reaction mixture was filtered. 7 M methanolic ammonia (3 mL, 21 mmol) was added and the resulting mixture was heated to 80° C. for 65 h. The reaction mixture was concentrated and the residue was purified by prep HPLC to give 93 mg of the title product (37% yield). 1H NMR (500 MHz, DMSO-d6) ppm 0.30-0.35 (m, 2H), 0.44-0.49 (m, 2H), 0.90 (m, 1H), 1.08-1.26 (m, 5H), 1.33-1.48 (m, 3H), 1.80 (m, 2H), 2.14 (s, 3H), 2.81-2.88 (m, 1H), 2.88-2.98 (m, 2H), 3.18 (s, 3H), 3.54-3.63 (m, 2H), 6.04 (d, 1H), 6.50 (s, 2H), 6.69 (dd, 1H), 7.14 (d, 1H); MS (ES+) m/z 382 [M+H]+.

Example 2

(1r,4r)-6'-[(3,3-Difluorocyclobutyl)methoxy]-4-methoxy-5''-methyl-3'H-dispiro[cyclohexane-1,2'-indene-1',2''-imidazol]-4''-amine

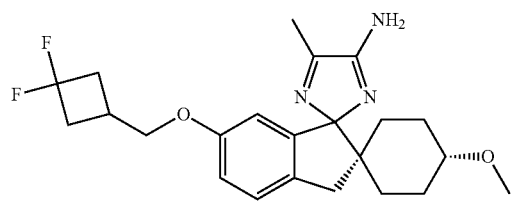

6'-[(3,3-difluorocyclobutyl)methoxy]-4-methoxy-5''-methyl-3'H-dispiro[cyclohexane-1,2'-indene-1',2''-imidazole]-4''(3''H)-thione (Intermediate 19, 106 mg, 0.24 mmol) was placed into a microwavave vial. Ammonia (7 M in MeOH) (2 mL, 14 mmol) was added, and the mixture was heated for 30 min at 90° C. in the MW reactor. The reaction mixture was concentrated, and ammonia (7 M in MeOH) (2 mL, 14 mmol) was added. The reaction mixture was heated by MW at 120° C. for 30 min. This cycle was repeated 5 times. The resulting mixture was concentrated, and the title compound (7 mg, 7% yield) was isolated by reverse phase preparative chromatography. $^1$H NMR (500 MHz, CDCl$_3$) ppm 1.07-1.17 (m, 1H) 1.27-1.44 (m, 3H) 1.63-1.76 (m, 2H) 1.95-2.08 (m, 2H) 2.43-2.46 (m, 3H) 2.46-2.50 (m, 1H) 2.53-2.61 (m, 1H) 2.65 (s, 2H) 2.67-2.73 (m, 2H) 3.04-3.12 (m, 2H) 3.13-3.20 (m, 1H) 3.34 (s, 3H) 3.92 (t, 2H) 6.37 (d, 1H) 6.86 (dd, 1H) 7.25 (d, 1H) 8.33 (s, 2H); MS (ES+) m/z 418 [M+H]$^+$.

Example 3

(1r,4r)-6'-(Cyclopropylmethoxy)-4-methoxy-5''-methyl-3'H-dispiro[cyclohexane-1,2'-indene-1',2''-imidazol]-4''-amine

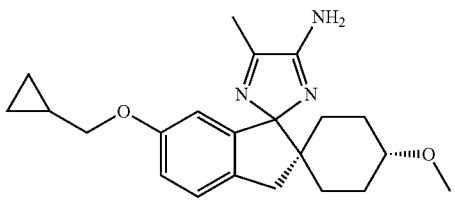

Di-tert-butyl [(1r,4r)-6'-bromo-4-methoxy-5''-methyl-3'H-dispiro[cyclohexane-1,2'-indene-1',2''-imidazol]-4''-yl]imidodicarbonate (Intermediate 9, 522 mg, 0.91 mmol), di-tert-butyl(2',4',6'-triisopropyl-3-methoxy-6-methylbiphenyl-2-yl)phosphine (26 mg, 0.05 mmol), allylpalladium chloride dimer (7 mg, 0.02 mmol) and Cs$_2$CO$_3$ (443 mg, 1.36 mmol) were weighed into a tube. The headspace was evacuated and refilled with argon. Toluene (3 mL) and cyclopropylmethanol (0.143 mL, 1.81 mmol) were added and the mixture was heated to 90° C. for 2 h and 40 min. The reaction mixture was filtered and 7 M methanolic ammonia (3.9 mL, 27 mmol) was added. The resulting solution was heated to 85° C. for 15 h. The mixture was concentrated and purified by flash column chromatography using gradient elution of 0-5% 0.2 M methanolic ammonia in DCM followed by preparative chromatography to give the title product (202 mg, 61% yield). $^1$H NMR (500 MHz, DMSO-d$_6$) ppm 0.2-0.3 (m, 2H), 0.5-0.5 (m, 2H), 0.9 (td, 1H), 1.1-1.3 (m, 3H), 1.3-1.5 (m, 3H), 1.7-1.9 (m, 2H), 2.1 (s, 3H), 2.8-2.9 (m, 1H), 2.9-3.0 (m, 2H), 3.2 (s, 3H), 3.6 (d, 2H), 6.0 (d, 1H), 6.5 (br. s., 2H), 6.7 (dd, 1H), 7.1 (d, 1H). MS (ES+) m/z 368 [M+H]$^+$.

Example 4

Separation of the isomers of (1r,4r)-6'-(cyclopropylmethoxy)-4-methoxy-5''-methyl-3'H-dispiro[cyclohexane-1,2'-indene-1',2''-imidazol]-4''-amine (1r,4r)-6'-(Cyclopropylmethoxy)-4-methoxy-5''-methyl-3'H-dispiro[cyclohexane-1,2'-indene-1',2''-imidazol]-4''-amine (Example 3, 147 mg, 0.40 mmol) divided in 3 portions was purified using a SFC Berger Multigram II system with a Chiralcel OD-H; 20*250 mm; 5 μm, column and a mobile phase consisting of 25% MeOH (containing 0.1% DEA) and 75% CO$_2$ at a flow rate of 50 mL/min to give:

Isomer 1 (1r,1'R,4R)-6'-(cyclopropylmethoxy)-4-methoxy-5''-methyl-3'H-dispiro[cyclohexane-1,2'-indene-1',2''-imidazol]-4''-amine with retention time 1.58 min (66 mg, 45% yield)

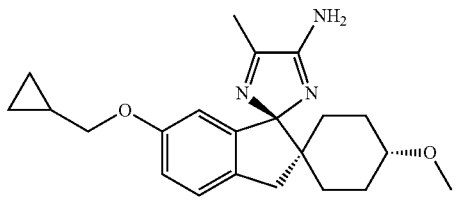 [SMILES: CO[C@H]1CC[C@]2(CC1)Cc1ccc(OCC3CC3)cc1[C@@]21N=C(C)C(N)=N1]

$^1$H NMR (500 MHz, DMSO-d$_6$) δ ppm 0.23-0.29 (m, 2H), 0.47-0.54 (m, 2H), 0.90 (td, 1H), 1.07-1.26 (m, 3H), 1.34-1.47 (m, 3H), 1.80 (d, 2H), 2.14 (s, 3H), 2.81-2.88 (m, 1H), 2.89-2.98 (m, 2H), 3.18 (s, 3H), 3.64 (d, 2H), 6.03 (d, 1H), 6.50 (s, 2H), 6.70 (dd, 1H), 7.14 (d, 1H). MS (ES+) m/z 368 [M+H]$^+$.

And Isomer 2 (1r,1'S,4S)-6'-(cyclopropylmethoxy)-4-methoxy-5''-methyl-3'H-dispiro[cyclohexane-1,2'-indene-1',2''-imidazol]-4''-amine with retention time 2.24 min (65 mg, 44% yield)

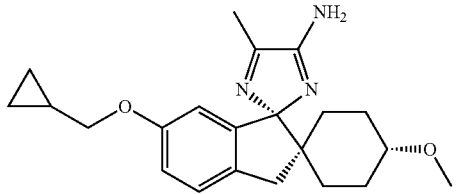 [SMILES: CO[C@H]1CC[C@]2(CC1)Cc1ccc(OCC3CC3)cc1[C@]21N=C(C)C(N)=N1]

$^1$H NMR (500 MHz, DMSO-d$_6$) ppm 0.26 (m, 2H), 0.51 (m, 2H), 0.90 (td, 1H), 1.07-1.26 (m, 3H), 1.34-1.48 (m, 3H), 1.80 (m, 2H), 2.14 (s, 3H), 2.80-2.88 (m, 1H), 2.88-2.98 (m, 2H), 3.18 (s, 3H), 3.64 (d, 2H), 6.04 (d, 1H), 6.50 (s, 2H), 6.70 (dd, 1H), 7.14 (d, 1H). MS (ES+) m/z 368 [M+H]$^+$.

Example 5

(1r,4r)-6'-[(2,2-Difluorocyclopropyl)methoxy]-4-methoxy-5''-methyl-3'H-dispiro[cyclohexane-1,2'-indene-1',2''-imidazol]-4''-amine

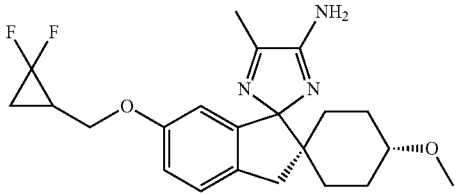

The title compound was prepared using the procedure described for Example 3, starting from di-tert-butyl [(1r,4r)-6'-bromo-4-methoxy-5''-methyl-3'H-dispiro[cyclohexane-1,2'-indene-1',2''-imidazol]-4''-yl]imidodicarbonate (Intermediate 9, 200 mg, 0.35 mmol), and (2,2-difluorocyclopropyl)

methanol (75 mg, 0.69 mmol) The product was purified by chromatography on a silica column (eluent 0-100% (7 M NH₃ in MeOH)/DCM 1:9 in DCM, followed by preparative HPLC to give the title compound (29 mg, 21% yield). ¹H NMR (500 MHz, DMSO-d₆) ppm 0.90 (br. s., 1H), 1.18 (m, 2H), 1.42 (m, 4H), 1.66 (m, 1H), 1.80 (d, 2H), 1.80 (m, 0H), 2.11 (m, 1H), 2.13 (s, 3H), 2.85 (d, 1H), 2.93 (m, 2H), 3.18 (s, 3H), 3.79 (d, 1H), 4.00 (m, 1H), 6.07 (d, 1H), 6.50 (br. s., 2H), 6.74 (dd, 1H), 7.16 (d, 1H); MS (ES+) m/z 404.09 [M+H]⁺.

Example 6

(1r,4r)-6'-(Cyclobutylmethoxy)-4-methoxy-5''-methyl-3'H-dispiro[cyclohexane-1,2'-indene-1',2''-imidazol]-4''-amine

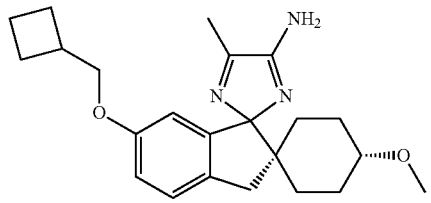

The title compound was prepared using the procedure described in Example 2, starting from (1r,4r)-6'-(cyclobutylmethoxy)-4-methoxy-5''-methyl-3'H-dispiro[cyclohexane-1,2'-indene-1',2''-imidazole]-4''(3''H)-thione (Intermediate 22, 140 mg, 0.35 mmol) The product was purified on a silica gel column (gradient elution of 0-100% (7 M NH₃ in MeOH/DCM 1:9) in DCM) followed by preparative chromatography to give the title compound (44 mg, 28% yield): ¹H NMR (500 MHz, DMSO-d₆) δ ppm 0.90 (t, 1H) 1.17 (m, 2H) 1.41 (m, 3H) 1.82 (m, 9H) 2.01 (m, 2H) 2.14 (s, 3H) 2.62 (m, 1H) 2.90 (m, 3H) 3.18 (s, 3H) 3.78 (m, 2H) 6.05 (s, 1H) 6.46 (br. s, 2H) 6.70 (d, 1H) 7.14 (d, 1H); MS (APCI+) m/z 382.2 [M+H]⁺.

Example 7

Separation of the Isomers of (1r,4r)-6'-(cyclobutylmethoxy)-4-methoxy-5''-methyl-3'H-dispiro[cyclohexane-1,2'-indene-1',2''-imidazol]-4''-amine The isomers of (1r,4r)-6'-(cyclobutylmethoxy)-4-methoxy-5''-methyl-3'H-dispiro[cyclohexane-1,2'-indene-1',2''-imidazol]-4''-amine (Example 6, 35 mg) were separated using a SFC Berger Multigram II system with a OD-H; 20*250 mm; 5 μm column, and a mobile phase consisting of 30% MeOH (containing 0.1% DEA) and 70% CO₂ at a flow rate of 50 mL/min to give:

Isomer 1: (1r,1'R,4R)-6'-(cyclobutylmethoxy)-4-methoxy-5''-methyl-3'H-dispiro[cyclohexane-1,2'-indene-1',2''-imidazol]-4''-amine (12 mg, 34% yield) with retention time 2.1 min

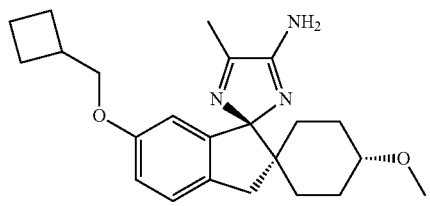 [SMILES: CO[C@H]1CC[C@]2(CC1)Cc1ccc(OCC3CCC3)cc1[C@@]21N=C(C)C(N)=N1]

¹H NMR (500 MHz, DMSO-d₆) δ ppm 0.90 (d, 1H), 1.14 (d, 2H), 1.41 (m, 3H), 1.82 (m, 6H), 2.01 (m, 2H), 2.15 (s, 3H), 2.62 (m, 1H), 2.90 (m, 3H), 3.18 (s, 3H), 3.78 (dd, 2H), 6.05 (d, 1H), 6.50 (br. s., 2H), 6.70 (dd, 1H), 7.14 (d, 1H), MS (APCI+) m/z 382 [M+H]⁺.
and And Isomer 2: (1r,1'S,4S)-6'-(cyclobutylmethoxy)-4-methoxy-5''-methyl-3'H-dispiro[cyclohexane-1,2'-indene-1',2''-imidazol]-4''-amine (12 mg, 34% yield) with Retention Time 5.0 Min

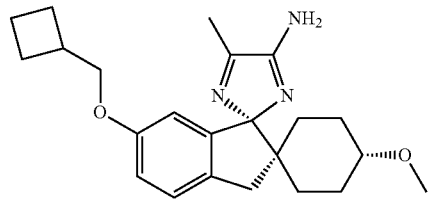

¹H NMR (500 MHz, DMSO-d₆) ppm 0.90 (m, 1H), 1.18 (m, 2H), 1.43 (m, 3H), 1.82 (m, 6H), 2.01 (m, 2H), 2.15 (s, 3H), 2.62 (m, 1H), 2.89 (m, 3H), 3.18 (s, 3H), 3.78 (dd, 2H), 6.05 (d, 1H), 6.50 (s, 2H), 6.70 (dd, 1H), 7.14 (d, 1H), MS (APCI+) m/z 382 [M+H]⁺.

Example 8

(1r,4r)-6'-(2-Cyclopropylethoxy)-4-methoxy-5''-methyl-3'H-dispiro[cyclohexane-1,2'-indene-1',2''-imidazol]-4''-amine

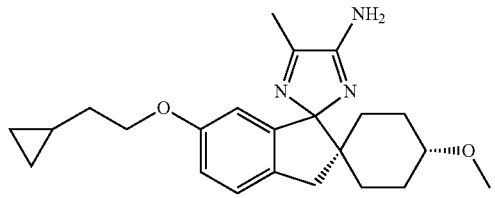

The head space above a mixture of di-tert-butyl [(1r,4r)-6'-bromo-4-methoxy-5''-methyl-3'H-dispiro[cyclohexane-1,2'-indene-1',2''-imidazol]-4''-yl]imidodicarbonate (Intermediate 9, 210 mg, 0.36 mmol), di-tert-butyl(2',4',6'-triisopropyl-3-methoxy-6-methylbiphenyl-2-yl)phosphine (10 mg, 0.02 mmol), allylpalladium chloride dimer (2.7 mg, 7.3 μmmol), cesium carbonate (178 mg, 0.55 mmol) and 2-cyclopropylethanol (63 mg, 0.73 mmol) was evacuated and refilled with argon. Toluene (1.3 mL) was added and the mixture was heated at 90° C. for 3 days. After another two days at r.t. the reaction mixture was filtered through a syringe filter. The filter was washed with 7 M ammonia in methanol (1.56 mL, 10.9 mmol). More 7 M ammonia in methanol (1.56 mL, 10.9 mmol) was added and the resulting solution was heated at 85° C. for 24 h. After cooling to r.t. the mixture was concentrated. The residue was partitioned between EtOAc and 2 M aq. citric acid. The phases were separated and the organic layer was extracted twice with 2 M aq. citric acid. The organic layer was discarded. The aqueous citric acid phases were basified with NaOH (50% aq.) and extracted twice with EtOAc. The organic phase was treated with active charcoal, dried (Na₂SO₄), filtered through diatomaceous earth and concentrated. Purification by flash silica gel chromatography, using a gradient of CHCl$_3$/MeOH (20:1-15:1-10:1) gave the title compound (56 mg, 40% yield). $^1$H NMR (500 MHz, DMSO-d$_6$) δ ppm 0.02-0.12 (m, 2H), 0.34-0.45 (m, 2H), 0.72-0.84 (m, 1H), 0.90 (td, 1H), 1.07-1.27 (m, 2H), 1.35-1.48 (m, 3H), 1.53 (q, 2H), 1.80 (d, 2H), 2.15 (s, 3H), 2.81-2.88 (m, 1H), 2.88-2.98 (m, 2H), 3.18 (s, 3H), 3.80-3.91 (m, 2H), 6.06 (d, 1H), 6.50 (s, 2H), 6.71 (dd, 1H), 7.15 (d, 1H); MS (ES+) m/z 382.1 [M+H]$^+$.

BIOLOGICAL ASSAYS

The level of activity of the compounds was tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in 50 mM Glycine pH 2.5, adjusted to pH 7.4 with 1 M Tris and had a purity of 40%.

The enzyme (truncated form) was diluted to 6 μg/mL (stock 1.3 mg/mL) and the TruPoint BACE1 Substrate to 200 nM (stock 120 μM) in reaction buffer (NaAcetate, chaps, triton x-100, EDTA pH4.5). Enzyme and compound in dimethylsulphoxide (final DMSO concentration 5%) was mixed and pre-incubated for 10 minutes at RT. Substrate was then added and the reaction was incubated for 15 minutes at RT. The reaction was stopped with the addition of 0.35 vol Stop solution (NaAcetate, pH 9). The fluorescence of the product was measured on a Victor II plate reader with excitation wavelengths of 340-485 nm and emission wavelengths of 590-615 nm. The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer) or by a saturating dose of a known inhibitor, 2-amino-6-[3-β-methoxyphenyl)phenyl]-3,6-dimethyl-5H-pyrimidin-4-one. A control inhibitor was also used in dose response assays and had an IC50 of ~150 nM.

Diluted TR-FRET Assay

Compounds with a high affinity were further tested in a diluted TR-FRET assay, conditions as described above for the TR-FRET assay, but with 50 times less enzyme and a 6.5 h long reaction time at r.t. in the dark.

sAPPβ Release Assay

SH-SY5Y cells were cultured in DMEM/F-12 with Glutamax, 10% FCS and 1% non-essential amino acids and cryopreserved and stored at −140° C. at a concentration of 7.5–9.5×10$^6$ cells per vial. Thaw cells and seed at a conc. of around 10000 cells/well in DMEM/F-12 with Glutamax, 10% FCS and 1% non-essential amino acids to a 384-well tissue culture treated plate, 1004, cell susp/well. The cell plates were then incubated for 7-24 h at 37° C., 5% CO$_2$. The cell medium was removed, followed by addition of 30 μL compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% CO$_2$. Meso Scale Discovery (MSD) plates were used for the detection of sAPPβ release. MSD sAPPβ plates were blocked in 1% BSA in Tris wash buffer (40 μL/well) for 1 h on shake at r.t. and washed 1 time in Tris wash buffer (40 μL/well). 20 μL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 μL detection antibody was added (1 nM) per well followed by incubation with shaking at r.t. for 2 h and then discarded. 40 μL Read Buffer was added per well and the plates were read in a SECTOR Imager.

ATP Assay

As indicated in the sAPPβ release assay, after transferring 20 μL medium from the cell plates for sAPPβ detection, the plates were used to analyse cytotoxicity using the ViaLight™ Plus cell proliferation/cytotoxicity kit from Cambrex BioScience that measures total cellular ATP. The assay was performed according to the manufacture's protocol. Briefly, 10 μL cell lysis reagent was added per well. The plates were incubated at r.t. for 10 min. Two min after addition of 25 μL reconstituted ViaLight™ Plus ATP reagent, the luminescence was measured. Tox threshold is a signal below 75% of the control.

Results

Typical IC$_{50}$ values for the compounds of the present invention are in the range of about 0.1 to about 100,000 nM. Biological data on particular example compounds is given below in Table 1.

TABLE 1

| Example | IC$_{50}$ in TR-FRET assay (nM) | IC$_{50}$ in sAPPβ release assay (nM) | Example | IC$_{50}$ in TR-FRET assay (nM) | IC$_{50}$ in sAPPβ release assay (nM) |
|---|---|---|---|---|---|
| 1 | 18$^a$ | 2.8 | 2 | 50 | 8.4 |
| 3 | 7.4$^a$ | 1.6 | 4, isomer 1 | 3.7$^a$ | 0.9 |
| 4, isomer 2 | >5000 | not tested | 5 | 13$^a$ | 2.3 |
| 6 | 6.1$^a$ | 1.5 | 7, isomer 1 | 4.5$^a$ | 1.3 |
| 7, isomer 2 | >4900 | not tested | 8 | 3.7$^a$ | 0.8 |

$^a$IC$_{50}$ from the diluted FRET assay.

The invention claimed is:

1. A compound of Formula 1

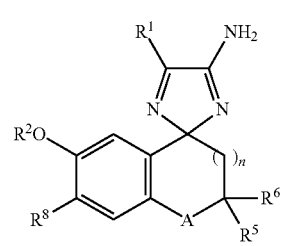

wherein

A is —O—, or —CH$_2$—;

n is 0 or 1;

R$^1$ is C$_{1-6}$alkyl or C$_{1-6}$haloalkyl;

R$^2$ is C$_{1-6}$alkyl, or C$_{1-6}$haloalkyl; wherein said C$_{1-6}$alkyl or C$_{1-6}$haloalkyl is substituted with one to three groups independently selected from C$_{3-6}$halocycloalkyl;

R$^5$ and R$^6$ is independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, $C_{1-6}$alkyl, $C_{1-6}$haloalkyl, or cyano;

or $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl, $C_{1-6}$haloalkyl, cyano, or $OR^7$;

$R^7$ is independently hydrogen, $C_{1-6}$alkyl, $C_{1-6}$haloalkyl, or $C_{0-6}$alkyl$C_{3-6}$cycloalkyl;

$R^8$ is hydrogen, halogen or methyl;

as a free base or a pharmaceutically acceptable salt thereof.

2. A compound selected from the group consisting of:
(1r,4r)-4-Methoxy-5"-methyl-6'-[(1-methylcyclopropyl)methoxy]-3'H-dispiro[cyclohexane-1,2'-indene-1',2"-imidazol]-4"-amine;
(1r,4r)-6'-[(3,3-Difluorocyclobutyl)methoxy]-4-methoxy-5"-methyl-3'H-dispiro[cyclohexane-1,2'-indene-1',2"-imidazol]-4"-amine;
(1r,4r)-6'-(Cyclopropylmethoxy)-4-methoxy-5"-methyl-3'H-dispiro[cyclohexane-1,2'-indene-1',2"-imidazol]-4"-amine;
(1r,1'R,4R)-6'-(Cyclopropylmethoxy)-4-methoxy-5"-methyl-3'H-dispiro[cyclohexane-1,2'-indene-1',2"-imidazol]-4"-amine;
(1r,1'S,4S)-6'-(Cyclopropylmethoxy)-4-methoxy-5"-methyl-3'H-dispiro[cyclohexane-1,2'-indene-1',2"-imidazol]-4"-amine;
(1r,4r)-6'-[(2,2-Difluorocyclopropyl)methoxy]-4-methoxy-5"-methyl-3'H-dispiro[cyclohexane-1,2'-indene-1',2"-imidazol]-4"-amine;
(1r,1'R,4R)-6'-(Cyclobutylmethoxy)-4-methoxy-5"-methyl-3'H-dispiro[cyclohexane-1,2'-indene-1',2"-imidazol]-4"-amine;
(1r,1'S,4S)-6'-(Cyclobutylmethoxy)-4-methoxy-5"-methyl-3'H-dispiro[cyclohexane-1,2'-indene-1',2"-imidazol]-4"-amine, and
(1r,4r)-6'-(2-Cyclopropylethoxy)-4-methoxy-5"-methyl-3'H-dispiro[cyclohexane-1,2'-indene-1',2"-imidazol]-4"-amine, or a pharmaceutically acceptable salt of any foregoing compound.

3. The compound or pharmaceutically acceptable salt thereof according to claim 2, wherein said compound is selected from:
(1r,4r)-6'-(Cyclopropylmethoxy)-4-methoxy-5"-methyl-3'H-dispiro[cyclohexane-1,2'-indene-1',2"-imidazol]-4"-amine:

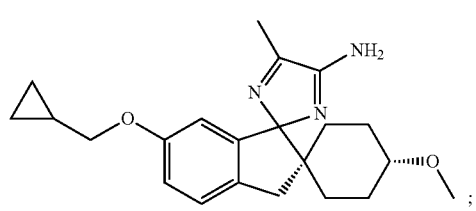

(1r,1'R,4R)-6'-(cyclopropylmethoxy)-4-methoxy-5"-methyl-3'H-dispiro[cyclohexane-1,2'-indene-1',2"-imidazol]-4"-amine:

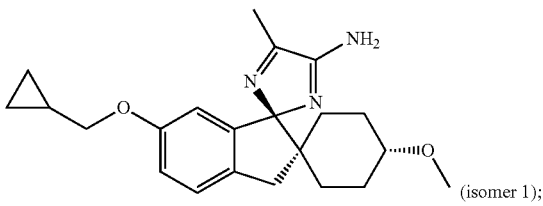 [SMILES: CO[C@H]1CC[C@]2(CC1)Cc1ccc(OCC3CC3)cc1[C@@]21N=C(C)C(N)=N1]

(isomer 1);

and
(1r,1'S,4S)-6'-(cyclopropylmethoxy)-4-methoxy-5"-methyl-3'H-dispiro[cyclohexane-1,2'-indene-1',2"-imidazol]-4"-amine:

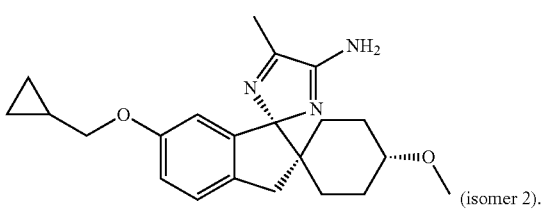 [SMILES: CO[C@H]1CC[C@]2(CC1)Cc1ccc(OCC3CC3)cc1[C@]21N=C(C)C(N)=N1]

(isomer 2).

4. A compound selected from the group consisting of:
(1r,4r)-4-Methoxy-5"-methyl-6'-[(1-methylcyclopropyl)methoxy]-3'H-dispiro[cyclohexane-1,2'-indene-1',2"-imidazol]-4"-amine;
(1r,4r)-6'-[(3,3-Difluorocyclobutyl)methoxy]-4-methoxy-5"-methyl-3'H-dispiro[cyclohexane-1,2'-indene-1',2"-imidazol]-4"-amine;
(1r,4r)-6'-(Cyclopropylmethoxy)-4-methoxy-5"-methyl-3'H-dispiro[cyclohexane-1,2'-indene-1',2"-imidazol]-4"-amine;
(1r,1'R,4R)-6'-(Cyclopropylmethoxy)-4-methoxy-5"-methyl-3'H-dispiro[cyclohexane-1,2'-indene-1',2"-imidazol]-4"-amine;
(1r, 1'S,4S)-6'-(Cyclopropylmethoxy)-4-methoxy-5"-methyl-3'H-dispiro[cyclohexane-1,2'-indene-1',2"-imidazol]-4"-amine;
(1r,4r)-6'-[(2,2-Difluorocyclopropyl)methoxy]-4-methoxy-5"-methyl-3'H-dispiro[cyclohexane-1,2'-indene-1',2"-imidazol]-4"-amine; and
(1r,4r)-6'-(2-Cyclopropylethoxy)-4-methoxy-5"-methyl-3'H-dispiro[cyclohexane-1,2'-indene-1',2"-imidazol]-4"-amine, or a pharmaceutically acceptable salt of any foregoing compound.

5. A pharmaceutical composition comprising as active ingredient a therapeutically effective amount of a compound according to any one of claims 1, 2, 3 and 4, or a pharmaceutically acceptable salt thereof, in association with at least one pharmaceutically acceptable excipient, carrier or diluent.

6. A method of treating Alzheimer's Disease in a patient in need thereof, comprising administering to said patient a therapeutically effective amount of a compound according to any one of claims 1, 2, 3 and 4, or a pharmaceutically acceptable salt thereof.

7. A method of treating an Aβ-related pathology in a patient in need thereof, comprising administering to said patient a therapeutically effective amount of a compound according to any one of claims 1, 2, 3 and 4, or a pharmaceutically acceptable salt thereof, and at least one cognitive enhancing agent, memory enhancing agent, or cholinesterase inhibitor, wherein said Aβ-related pathology is Alzheimer's Disease.

* * * * *